(12) United States Patent
Hayashi et al.

(10) Patent No.: US 9,279,762 B2
(45) Date of Patent: Mar. 8, 2016

(54) APPARATUS AND METHOD FOR MEASURING SEMICONDUCTOR CARRIER LIFETIME

(75) Inventors: Kazushi Hayashi, Kobe (JP); Hiroyuki Takamatsu, Kobe (JP); Yoshito Fukumoto, Kobe (JP); Shingo Sumie, Kobe (JP)

(73) Assignees: Kobe Steel, Ltd., Hyogo (JP); Kobelco Research Institute, Inc., Hyogo (JP)

( * ) Notice: Subject to any disclaimer, the term of this patent is extended or adjusted under 35 U.S.C. 154(b) by 822 days.

(21) Appl. No.: 13/500,305

(22) PCT Filed: Oct. 1, 2010

(86) PCT No.: PCT/JP2010/005920
§ 371 (c)(1),
(2), (4) Date: Apr. 5, 2012

(87) PCT Pub. No.: WO2011/043048
PCT Pub. Date: Apr. 14, 2011

(65) Prior Publication Data
US 2012/0203473 A1 Aug. 9, 2012

(30) Foreign Application Priority Data

Oct. 6, 2009 (JP) ................................ 2009-232880
Apr. 28, 2010 (JP) ................................ 2010-103331

(51) Int. Cl.
*G01N 21/31* (2006.01)
*G01N 21/3563* (2014.01)
*H01L 21/66* (2006.01)

(52) U.S. Cl.
CPC ............ *G01N 21/3151* (2013.01); *G01N 21/31* (2013.01); *H01L 22/14* (2013.01); *G01N 2021/3568* (2013.01); *H01L 2924/0002* (2013.01)

(58) Field of Classification Search
CPC .............. G01N 21/31; G01N 21/3151; G01N 2021/3568; H01L 22/14; H01L 2924/00; H01L 2924/0002
See application file for complete search history.

(56) References Cited

U.S. PATENT DOCUMENTS 5,081,414 A * 1/1992 Kusama et al. .......... 324/750.03
5,196,786 A 3/1993 Usami et al.
(Continued)

FOREIGN PATENT DOCUMENTS

| JP | 57-054338 | 3/1982 |
| JP | 03-278442 | 12/1991 |

(Continued)

OTHER PUBLICATIONS

Flohr et al., "Determination of minority-carrier lifetime and surface recombination velocity by optical-beam-induced-current measurements at different light wavelengths" Journal of Applied Physics 66, 3060 (1989).*
Ogita, "Bulk lifetime and surface recombination velocity measurement method in semiconductor wafers" Journal of Applied Physics 79, 6954 (1996).*
Korean Office Action for corresponding KR Application No. 10-2012-7011662, Apr. 5, 2013.
(Continued)

*Primary Examiner* — Alexander Satanovsky
*Assistant Examiner* — John Kuan
(74) *Attorney, Agent, or Firm* — Studebaker & Brackett PC

(57) ABSTRACT

In a semiconductor carrier lifetime measuring apparatus A1 of the present invention, at least two types of light having mutually different wavelengths are irradiated onto a semiconductor X to be measured, a predetermined measurement wave is irradiated onto the semiconductor X to be measured, a reflected wave of the measurement wave that has been reflected by the semiconductor X to be measured or a transmitted wave of the measurement wave that has transmitted through the semiconductor X to be measured is detected, and the carrier lifetime in the semiconductor X to be measured is obtained based on the detection results so as to minimize the error. Accordingly, the semiconductor carrier lifetime measuring apparatus A1 configured as described above can more accurately measure the carrier lifetime.

10 Claims, 15 Drawing Sheets

(56) References Cited

U.S. PATENT DOCUMENTS

| | | | | |
|---|---|---|---|---|
| 5,438,276 A | * | 8/1995 | Kawata et al. | 324/754.31 |
| 5,760,597 A | * | 6/1998 | Yoshida et al. | 324/754.23 |
| 6,512,384 B1 | * | 1/2003 | Lagowski et al. | 324/754.23 |

FOREIGN PATENT DOCUMENTS

| | | |
|---|---|---|
| JP | 07-240450 | 9/1995 |
| JP | 2000-171415 | 6/2000 |
| JP | 2004-006756 | 1/2004 |

OTHER PUBLICATIONS

International Search Report for corresponding International Application No. PCT/JP2010/005920, Dec. 28, 2010.

A. Buczkowski et al, Bulk and surface components of recombination Lifetime based on a two-laser microwave reflection technique, J. Appl. Phys. 1991, p. 6495, vol. 69, (9).

International Preliminary Report on Patentability (Chapter 1) with translation of Written Opinion for corresponding International Application No. PCT/JP2010/005920, May 18, 2012.

* cited by examiner

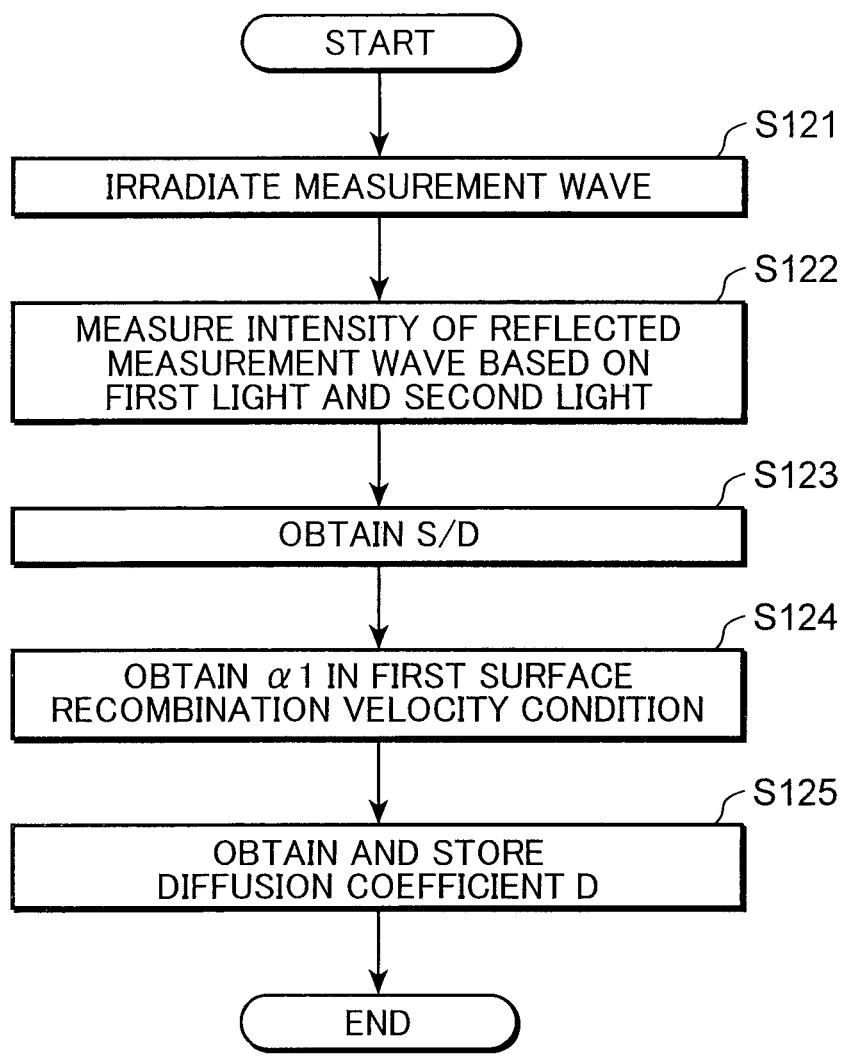

APPARATUS AND METHOD FOR MEASURING SEMICONDUCTOR CARRIER LIFETIME

TECHNICAL FIELD

The present invention relates to a semiconductor carrier lifetime measuring apparatus and a semiconductor carrier lifetime measuring method for measuring a carrier lifetime of a semiconductor.

BACKGROUND ART

Pursuant to the development of electronics in recent years, semiconductor products are being utilized in various fields. Since semiconductor products are generally manufactured from a semiconductor wafer, the quality management of semiconductor wafers is important to achieve enhanced performance of the semiconductor products. As one index of evaluating the quality of a semiconductor wafer, there is the life (lifetime) of a carrier in the semiconductor. Particularly in recent years, photovoltaic (PV) cells are attracting attention as a clean energy source. With these photovoltaic cells, it is important for the carriers (electrons and holes) that are generated by irradiation of light to reach the electrode without any recombining midway in order to achieve high photoelectric conversion efficiency. Thus, it is also important to evaluate the carrier lifetime in a PV semiconductor wafer. Base on the evaluation of the carrier lifetime, it is possible to improve the yield of photovoltaic cells by sorting, during the production process, the PV semiconductor wafers that are unable to achieve the required specification (spec). Consequently, it is also possible to achieve cost reduction.

As one method of measuring the carrier lifetime, a microwave photoconductive decay method (μ-PCD method) is known. The microwave photoconductive decay method is a method which generates excess carriers by irradiating light onto a semiconductor (semiconductor sample, measured sample) to be measured, and detects the process of the excess carriers becoming recombined and extinct in the carrier lifetime that is determined based on the physicality of the semiconductor sample based on the time change of reflectance or the time change of transmittance of the microwave. Since the generation of excess carriers increases the conductivity of the semiconductor, with the microwave that is irradiated onto the site (portion, region) of the semiconductor in which excess carriers were generated via photoexcitation, its reflectance or transmittance changes in accordance with the density of the excess carriers. This microwave photoconductive decay method is used for measuring the carrier lifetime by utilizing the foregoing phenomenon.

Generally speaking, crystalline imperfection exists on the surface of the semiconductor wafer, and so-called surface recombination where carriers recombine on the semiconductor surface will consequently arise. Thus, the measurement results of the carrier lifetime not only include the carrier lifetime (bulk carrier lifetime) based on the internal recombination of the semiconductor wafer, but also include the carrier lifetime (surface carrier lifetime) based on the foregoing surface recombination. The bulk carrier lifetime is important in the quality management of the semiconductor wafers, and the carrier lifetime based on surface recombination results in a measurement error. Thus, normally, the semiconductor sample is subject to heat treatment prior to being measured and an oxide film is formed on the semiconductor sample surface so as to inhibit the generation of the surface recombination, or the semiconductor sample is dipped in a solution containing, for example, iodine prior to being measured so that so-called dangling bonds or the like that cause surface recombination are passivated. This kind of pretreatment that is performed in advance is troublesome and time-consuming, and the semiconductor wafer may be subject to performance loss due to the heat treatment or the semiconductor wafer may be contaminated due as a result of being dipped in a chemical. Thus, a method of more easily measuring the bulk carrier lifetime in the semiconductor wafer is being demanded, and, for instance, thereafter the technologies disclosed in Patent Document 1 to Patent Document 3, and the technology disclosed in Non-Patent Document 1.

The carrier lifetime measuring method disclosed in Patent Document 1 is a carrier lifetime measuring method based on the photoexcitation method of injecting excess carriers, via photoexcitation, to the vicinity of the surface of the semiconductor substrate in a state of thermal equilibrium, and detecting and measuring the temporal change in the amount of reflection of the microwave upon viewing the decay process of the excess carrier concentration as the change in conductance, wherein an insulating film is provided to the surface of the semiconductor substrate prior to measuring the carrier lifetime, forming a charge layer thereon, and using a corona discharge for accumulating positive or negative charge on the insulating film surface provided to the semiconductor substrate in order to form the charge layer.

With the carrier lifetime measuring method disclosed in Patent Document 1, since the charge layer, which is generated by a corona discharge, below the insulating layer will easily discharge, surface recombination will occur during the measurement of the lifetime of the semiconductor carrier, and it is thereby difficult to accurately measure the lifetime of the semiconductor carrier.

Thus, the semiconductor carrier lifetime measuring apparatus disclosed in Patent Document 2 is a semiconductor carrier lifetime measuring apparatus which measures the semiconductor carrier lifetime by measuring the change in the reflected or transmitted wave of a predetermined measurement wave that was irradiated onto the semiconductor when pulsed light is irradiated onto the semiconductor, and comprises a waveguide for guiding the measurement wave to the surface of the semiconductor, and a first electrode which is provided to a portion of the waveguide that is adjacent to the semiconductor or in the vicinity thereof, and in which a predetermined voltage is applied and causes a corona discharge at least during the measurement of the change in the reflected wave or the transmitted wave of the measurement wave.

Moreover, with the lifetime measuring method disclosed in Non-Patent Document 1, at least two types of pulsed light having different wavelengths and different lengths of penetration are irradiated onto a semiconductor, photoexcited carriers are thereby generated in the semiconductor, and a temporal relative change in the reflected wave or the transmitted wave which decreases based on the recombination of the photoexcited carriers and the difference thereof are thereafter detected. According to the lifetime measuring method disclosed in Non-Patent Document 1, it is possible to analytically separate the surface carrier extinction and the bulk carrier extinction regardless of the surface combination velocity of the wafer surface. Non-Patent Document 1 describes that, consequently, the bulk carrier lifetime can be extracted.

Meanwhile, the semiconductor carrier measuring apparatus disclosed in foregoing Patent Document 2 is advantageous in that it is not necessary to perform any pretreatment process in advance such as heating or oxide film formation, and that it is possible to maintain the charged state in the measurement wave irradiated portion of the semiconductor during the measurement thereof, but a measurement error will occur if the charged state changes due to a discharge during the measurement. Moreover, much time is required for stabilizing the charged state, and the semiconductor carrier measuring apparatus disclosed in Patent Document 2 is not suitable for measuring the carrier lifetime and sorting the semiconductor wafers during the production process; that is, in the production line. Due to the foregoing reasons, there is room for improvement in the semiconductor carrier measuring apparatus disclosed in Patent Document 2.

Moreover, with the surface recombination velocity as S and the diffusion coefficient as D, the value that is obtained from the measurement results of the lifetime measuring method disclosed in foregoing Non-Patent Document 1 is S/D, and the lifetime measuring method disclosed in Non-Patent Document 1 obtains the surface recombination velocity S by assuming $D=30\ cm^2/s$, and thereby obtains the carrier lifetime. Nevertheless, when the carrier concentrations of electrodes and holes are n and p, respectively, and the diffusion coefficients of electrodes and holes are Dn and Dp, respectively, the actual diffusion coefficient is given as $(n+p)/(n/Dp+p/Dn)$, and this is dependent on the carrier concentration or conduction, and is not constant. In addition, when the surface recombination velocity S is relatively large such as when pretreatment is not performed in advance, the measured (observed) carrier lifetime will be small in comparison to the bulk carrier lifetime, and its change will also be small, thereby causing the measurement error to increase.

Meanwhile, the method of measuring the semiconductor wafer characteristics disclosed in Patent Document 3 is a method which irradiates a light beam or an electron beam onto one surface and/or another surface of a semiconductor wafer, and detects a conductive time change of the semiconductor wafer based on at least two types of different spatial distributions caused by the difference in the carrier excitation conditions of the excess carriers that were instantaneously excited by the irradiation of the light beam or the electron beam so as to separately measure the surface recombination velocity of one surface of the semiconductor wafer and the surface recombination velocity and the bulk lifetime of the other surface recombination velocity, respectively.

As described above, the methods disclosed in Patent Document 3 and Non-Patent Document 1 are methods that measure the carrier lifetime by using the difference between the respective measurement results that are obtained based on mutually different conditions. Thus, when the difference between the respective measurement results is small, the number of significant figures in the difference between the respective measurement results will be small, and, consequently, it is difficult to accurately measure the carrier lifetime.

Patent Document 1: Japanese Patent Application Publication No. H7-240450
Patent Document 2: Japanese Patent Application Publication No. 2004-006756
Patent Document 3: Japanese Patent Application Publication No. S57-054338
Non-Patent Document 1: J. Appl. Phys. Vol. 69, (9), 6495 (1991)

SUMMARY OF THE INVENTION

The present invention was devised in view of the foregoing circumstances, and its object is to provide a semiconductor carrier lifetime measuring apparatus and a semiconductor carrier lifetime measuring method capable of more accurately measuring the carrier lifetime.

With the semiconductor carrier lifetime measuring apparatus and the semiconductor carrier lifetime measuring method according to the present invention, at least two types of light having mutually different wavelengths are irradiated onto a semiconductor to be measured, a predetermined measurement wave is irradiated onto the semiconductor to be measured, a reflected wave of the measurement wave that has been reflected by the semiconductor to be measured or a transmitted wave of the measurement wave that has transmitted through the semiconductor to be measured is detected, and a carrier lifetime in the semiconductor to be measured is obtained based on the foregoing detection results so as to minimize any error. Accordingly, the semiconductor carrier lifetime measuring apparatus and the semiconductor carrier lifetime measuring method configured as described above can more accurately measure the carrier lifetime.

The foregoing and other objects, features and advantages of the present invention shall become clear from the following detailed description and appended drawings.

BRIEF DESCRIPTION OF THE DRAWINGS

FIG. 15 is a flowchart showing the operation of the semiconductor carrier lifetime measuring apparatus of the third embodiment in cases of obtaining the diffusion coefficient.

MODE FOR CARRYING OUT THE INVENTION

Figure 1:
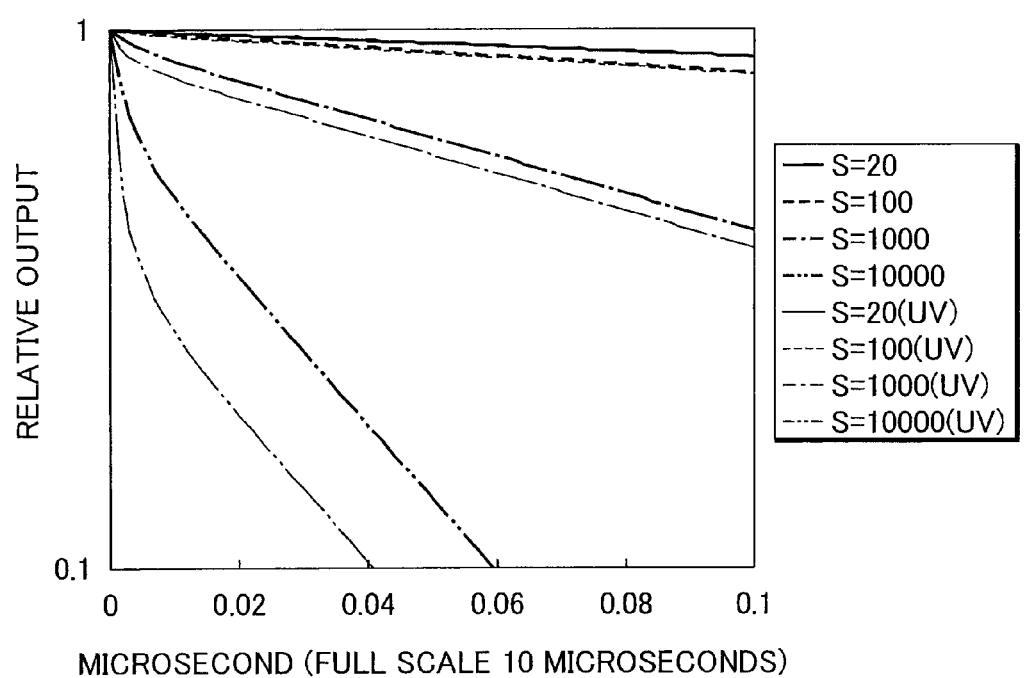
FIG. 1 is a diagram showing the surface recombination dependency of the time change of the relative output in the reflected wave of the measurement wave regarding each of the two lights having mutually different wavelengths.

An embodiment of the present invention is now explained with reference to the drawings. Note that any configuration given the same reference numeral in the respective drawings indicate that it is the same configuration, and the explanation thereof is omitted as needed. Moreover, in this specification, a reference numeral without any suffix is used for collective designations, and a reference numeral with a suffix is used to indicate individual configurations.

(First Embodiment)

Figure 2:
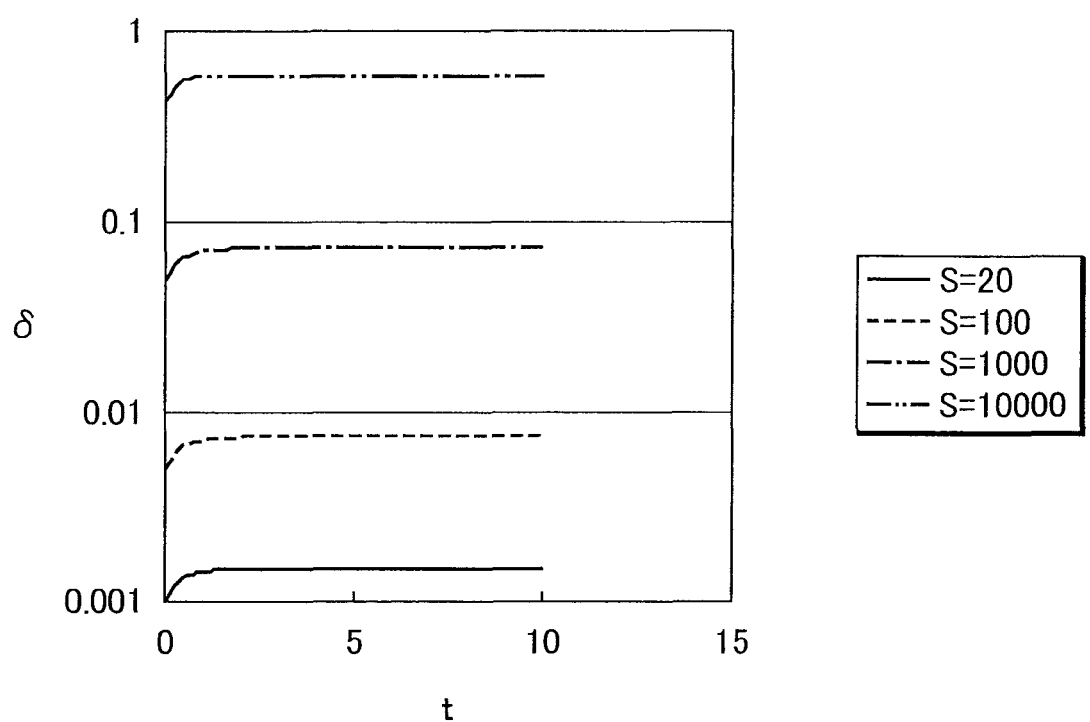
FIG. 2 is a diagram showing the time change of the relative output difference of the reflected wave of the measurement wave in each of the two lights having mutually different wavelengths.

The measurement principle in a carrier lifetime measuring apparatus of this embodiment is foremost explained. FIG. 1 is a diagram showing the surface recombination dependency of the time change of the relative output in the reflected wave of the measurement wave regarding each of the two lights having mutually different wavelengths. The horizontal axis of FIG. 1 is the elapsed time represented in μs (microsecond) units with the point of completion of the irradiation of each light as the origin, and the vertical axis shows the relative output (reflected wave relative intensity of the measurement wave). FIG. 1 shows, regarding infrared light (bold line) having a wavelength of 904 nm and ultraviolet light (thin line) having a wavelength of 349 nm, respectively, the time change of the relative output in the reflected wave of the measurement wave in the respective cases where the surface recombination velocity S is 20 (solid line), 100 (broken line), 1000 (chain line) and 10000 (chain double-dashed line). Here, δ is as defined in Formula 4 described later. FIG. 2 is a diagram showing the time change of the relative output difference of the reflected wave of the measurement wave in each of the two lights having mutually different wavelengths. The horizontal axis of FIG. 2 is the same as the horizontal axis of FIG. 1, and the vertical axis is the relative output difference δ of the reflected wave of the measurement wave in each light. FIG. 2 shows the time change of the relative output difference of the reflected wave of the measurement wave in each of the two lights having mutually different wavelengths in the respective cases where the surface recombination velocity S is 20 (solid line), 100 (broken line), 1000 (chain line) and 10000 (chain double-dashed line).

With the microwave photoconductive decay method, the intensity (relative output) of the reflected wave of the measurement wave will gradually decrease according to the lapse of time as shown in FIG. 1 due to the decrease in the excess carriers caused by the end of light irradiation. In addition, as shown in FIG. 1, the profile thereof is dependent on the wavelength of the light that is irradiated onto the semiconductor to be measured, and is further dependent on the surface recombination velocity S. In particular, when the surface recombination velocity S is 1000 or 10000, there is a considerable change in the cases of each light.

With respect to these measurement results, when the carrier lifetime that is actually observed in the measurement based on the microwave photoconductive decay method is $\tau 1$, the bulk carrier lifetime is $\tau b$, and the diffusion coefficient is D, Formula 1 is realized.

$$1/\tau 1 = 1/\tau b + \alpha^2 \times D \tag{1}$$

Here, α is given as the lowest order solution of the characteristic Formula 2 which defines α. Note that d is the thickness of the semiconductor in the region onto where light is irradiated.

$$(\alpha \times D/S) = \cot(\alpha \times d/2) \tag{2}$$

Thus, in cases where the surface recombination velocity condition is different, when the carrier lifetime that is actually observed in the measurement is $\tau 11$ and the α in this case is α1 in the first surface recombination velocity condition, and when the carrier lifetime that is actually observed in the measurement is $\tau 12$ and the α in this case is α2 in the second surface recombination velocity condition that is different from the first surface recombination velocity condition, Formula 1a and Formula 1b are realized.

$$1/\tau 11 = 1/\tau b + \alpha 1^2 \times D \tag{1a}$$

$$1/\tau 12 = 1/\tau b + \alpha 2^2 \times D \tag{1b}$$

Accordingly, Formula 3 is obtained by erasing the diffusion coefficient D from the foregoing two formulae; namely, Formula 1a and Formula 1b, and the bulk carrier lifetime $\tau b$ can be obtained without depending on the diffusion coefficient D.

$$\tau b = (\alpha 1^2 - \alpha 2^2)/(\alpha 1^2/\tau 12 - \alpha 2^2/\tau 11) \tag{3}$$

Based on this kind of measurement principle, the carrier lifetime measuring apparatus according to this embodiment can obtain the bulk carrier lifetime $\tau b$ by obtaining $\tau 11$, $\tau 12$, α1 and α2.

Here, foregoing $\tau 11$ and $\tau 12$ are values that are actually observed in the measurement. Meanwhile, α1 and α2 are values that are given by Formula 2. According to Formula 2, since the thickness d of the semiconductor can be measured, α1 and α2 can be obtained by obtaining D/S. Meanwhile, S/D as the reciprocal of D/S is a value having a correlation with the difference δ of the temporal relative change in the reflected wave of the measurement wave in each light, and S/D can be obtained based on the difference δ of the temporal relative change. Note that, more specifically, as described later with reference to Formula 4 and so on, S/D is evaluated based on the excitation measurement of two wavelengths. In addition, the difference δ of the temporal relative change is dependent on the surface recombination velocity as shown in FIG. 2, but becomes a substantially constant value in accordance with the lapse of time. Accordingly, α1 and α2 can also be obtained by obtaining the difference δ of the temporal relative change.

Moreover, in addition to the bulk carrier lifetime $\tau b$, the evaluation of the surface recombination velocity S which shows the surface carrier lifetime is also important in evaluating the semiconductor. This S can be obtained by multiplying (S/D) by D.

Figure 3:
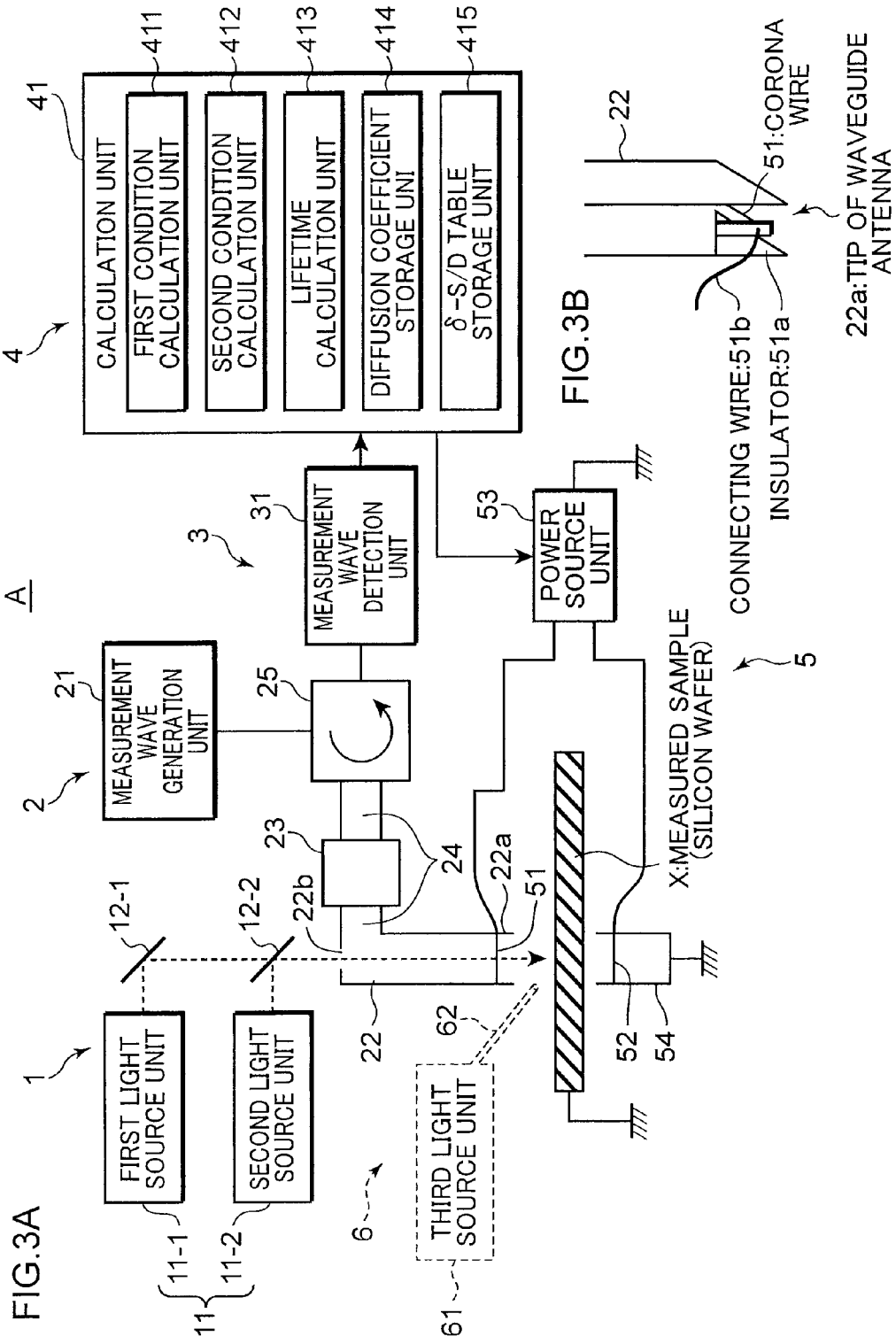
FIGS. 3A and 3B are diagrams showing the configuration of the semiconductor carrier lifetime measuring apparatus of the first embodiment.

The carrier lifetime measuring apparatus according to this embodiment is now explained in further detail. FIG. 3 are diagrams showing the configuration of the semiconductor carrier lifetime measuring apparatus of the first embodiment. FIG. 3A is a diagram showing the overall configuration, and FIG. 3B is a partial enlarged perspective view showing the tip part of the waveguide antenna.

The semiconductor carrier lifetime measuring apparatus A1 of this embodiment is configured by comprising, for example, as shown in FIG. 3A, a light irradiation unit 1, a measurement wave I/O unit 2, a detection unit 3, a calculation control unit 4, and a discharge unit 5.

The light irradiation unit 1 is a device for emitting at least two types of light having mutually different wavelengths onto a semiconductor wafer (measured sample) X, such as a silicon wafer, to be measured, in order to cause the lengths of penetration to be mutually different. With the semiconductor carrier lifetime measuring apparatus A1 of this embodiment, the light irradiation unit 1 is configured, as shown in FIG. 3A, so as to emit mutually different two types of light, and more specifically is configured by comprising a first light source unit 11-1 which emits a first light of a first wavelength according to the control of a calculation control unit 4, a first mirror 12-1 which directs the first light that was emitted from the first light source unit 11-1 toward the measured sample X and bends its light path approximately 90 degrees, and a second mirror 12-2 which directs a second light emitted from a second light source unit 11-2 according to the control of the calculation control unit 4 toward the measured sample X and bends its light path approximately 90 degrees.

The first and second light source units 11-1, 11-2 may be, for instance, a light source device or the like comprising a lamp and a wavelength filter, but in this embodiment, they are configured by comprising a laser beam source device which emits laser beams and is able to obtain a relatively large output. The first light and the second light are monochromatic light, and preferably their wavelength difference is large (of a wider interval) so as to generate a greater difference in the length of penetration (difference in the length of penetration of a wider space), and, for instance, the first light source unit 11-1 is a device which emits a laser beam of a predetermined wavelength in an infrared region; that is, an infrared laser beam, and the second light source unit 11-2 is a device which emits a laser beam of a predetermined wavelength in an ultraviolet region; that is an ultraviolet laser beam. Note that the second light source unit 11-2 may also be a device which emits a laser beam of a predetermined wavelength in a visible region; that is, a visible laser beam. The respective wavelengths of the first and second light source units 11-1, 11-2 are arbitrarily selected, for example, according to the type of the measured sample X. For example, if the measured sample X is a silicon wafer, in addition to the perspectives described above, from the perspective of efficiency of photoexcitation and cost reduction of the light source 11, the respective wavelengths of the first and second light source units 11-1, 11-2 are preferably a combination of 904 nm and 349 nm, or a combination of 904 nm and 523 nm. Since the first and second light generate carriers (electrons and holes) in the measured sample based on photoexcitation as a result of being irradiated onto the measured sample, and since the semiconductor carrier lifetime measuring apparatus A1 is an apparatus for measuring the lifetime (carrier lifetime) of the generated carriers, the first and second light preferably shift from a non-lit state to a lit-state in a stepwise manner, and, in this embodiment, for example, pulsed light, and more specifically, a pulsed laser beam, is used.

The first and second mirrors 12-1, 12-2 may be configured so that the second mirror 12-2 transmits the first light and disposed so that the first light, in which its light path was bent by the first mirror 12-1, reaches the measured sample via the second mirror 12-2, but in this embodiment, for instance, they are disposed so that a first light path of the first light in which its light path was bent by the first mirror 12-1 and a second light path of the second light in which its light path was bent by the second mirror 12-2 form a V-shape by intersecting at the light irradiated surface (light irradiated region) of the measured sample X.

The measurement wave I/O unit 2 is a device which irradiates a predetermined measurement wave onto the light irradiated surface of the measured sample X, and emits a measurement wave that was subject to a predetermined interaction with the measured sample X, and corresponds to an example of the measurement wave irradiation unit. With the semiconductor carrier lifetime measuring apparatus A1 of this embodiment, the measurement wave I/O unit 2 is configured, as shown in FIG. 3A, by comprising a measurement wave generation unit 21, a waveguide antenna 22, an E-H tuner 23, a waveguide 24, and a circulator 25.

The measurement wave generation unit 21 is a device which generates the predetermined measurement wave according to the control of the calculation control unit 4. With the semiconductor carrier lifetime measuring apparatus A1 of this embodiment, the predetermined measurement wave may be an electromagnetic wave since the conductivity change of the semiconductor that occurs during the course of generation/extinction of the carrier is extracted based on the intensity change of the measurement wave, in this embodiment it is a microwave, and the measurement wave generation unit 21 is configured by comprising a microwave oscillator which generates a microwave. The measurement wave generation unit 21 is connected to one terminal of the circulator 25, and the measurement wave emitted from the measurement wave generation unit 21 enters the circulator 25.

The circulator 25 has three or more terminals (ports), and is used for irreversibly outputting the input of one terminal to the other terminal in a cyclic manner. In this embodiment, the circulator 25 comprises three first to third terminals, and is an optical element which outputs the measurement wave, which entered the first terminal, to the second terminal, and outputs the measurement wave, which entered the second terminal, to the third terminal. The first terminal of the circulator 25 is connected to the measurement wave generation unit 21, its second terminal is connected to the waveguide 24, and its third terminal is connected to the measurement wave detection unit 31.

The waveguide 24 is a member which forms a propagation path for guiding the measurement wave, and its one end is connected to the second terminal of the circulator 25, and its other end is connected to the waveguide antenna 22. In this embodiment, since the measurement wave is a microwave, the waveguide 24 is a microwave waveguide.

The waveguide antenna 22 is an antenna which emits the measurement wave, which arrived by propagating through the waveguide 24, to the measured sample, and receives the measurement wave that interacted with the measured sample and guides this to the waveguide 24. The waveguide antenna 22 is disposed along the normal direction of the measured sample, and one end is connected to the waveguide 24 and the other end comprises an opening 22a. The opening 22a is an aperture for emitting the measurement wave to the measured sample and receiving the measurement wave that interacted with the measured sample. In addition, the one end of the waveguide antenna 22 comprises an opening 22b for guiding the first and second light emitted from the light irradiation unit 1 into the waveguide antenna 22. In this embodiment, since the measurement wave is a microwave, the waveguide antenna 22 is a microwave antenna.

The E-H tuner 23 is provided to the waveguide 24 between the circulator 25 and the waveguide antenna 22, and is a device which adjusts the magnetic field of the measurement wave so that the measurement wave that interacted with the measured sample can be better detected by the measurement wave detection unit 31.

The detection unit 3 is a device which detects the measurement wave that interacted with the measured sample and is configured, for example, by comprising a measurement wave detection unit 31 which detects the intensity of the measurement wave that interacted with the measured sample X. In this embodiment, since the measurement wave is a microwave, the measurement wave detection unit 31 is configured by comprising a microwave detector.

The calculation control unit 4 is a device which governs the overall control of the semiconductor carrier lifetime measuring apparatus A1 and is configured, for example, by comprising a microcomputer including a microprocessor, a memory and the like. In addition, the calculation control unit 4 comprises a calculation unit 41 which calculates the carrier lifetime based on the intensity of the measurement wave that interacted with the measured sample X that was detected by the measurement wave detection unit 31. The calculation unit 41 functionally comprises a first condition calculation unit 411, a second condition calculation unit 412, a lifetime calculation unit 413, a diffusion coefficient storage unit 414, and a δ-S/D table storage unit 415 as a result of, for example, executing the carrier lifetime calculation program for calculating the carrier lifetime based on the intensity of the reflected wave of the measurement wave (reflected measurement wave) that was detected by the measurement wave detection unit 31.

The first condition calculation unit 411 is used for obtaining the first difference of the temporal relative change in the reflected wave of the measurement wave that was detected by the detection unit 3 as a result of the light irradiation unit 1 irradiating the first and second light onto the measured sample X and the measurement wave I/O unit 2 irradiating the measurement wave onto the measured sample X when the measured sample X is in a first surface recombination velocity condition. More specifically, in this embodiment, the first condition calculation unit 411 obtains the first difference of the temporal relative change, obtains S/D in the first surface recombination velocity condition based on the obtained first difference, and obtains the diffusion coefficient D based on the S/D in the obtained first surface recombination velocity condition. The obtained diffusion coefficient D is stored in the diffusion coefficient storage unit 414 since it will be used subsequently for measuring a similar measured sample X.

The second condition calculation unit 412 is used for obtaining the second difference of the temporal relative change in the reflected wave of the measurement wave that was detected by the detection unit 3 as a result of the light irradiation unit 1 irradiating the first and second light onto the measured sample X and the measurement wave I/O unit 2 irradiating the measurement wave onto the measured sample X when the measured sample X is in a second surface recombination velocity condition that is different from the first surface recombination velocity condition. More specifically, in this embodiment, the second condition calculation unit 412 obtains the second difference of the temporal relative change, obtains S/D in the second surface recombination velocity condition based on the obtained second difference, and obtains the surface recombination velocity S based on the obtained S/D in the second surface recombination velocity condition and the diffusion coefficient D that was obtained by the first condition calculation unit 411.

The lifetime calculation unit 413 is used for obtained the bulk carrier lifetime τb based on the surface recombination velocity S that was obtained by the second condition calculation unit 412.

The diffusion coefficient storage unit 414 is used for storing the diffusion coefficient D that was obtained by the first condition calculation unit 412.

The δ-S/D table storage unit 415 is used for storing the δ-S/D table. The δ-S/D table is a so-called look-up table that shows the correspondence relationship of the δ value and the S/D value and, for example, is obtained and prepared in advance via simulation or the like. The difference δ of the temporal relative change is the natural logarithm value of the reflected measurement wave intensity based on the irradiation of the first light (long wavelength light) relative to the reflected measurement wave intensity based on the irradiation of the second light (short wavelength light) that were detected by the measurement wave detection unit 31 as shown in Formula 4.

$$\delta=\ln((\text{first light(long wavelength light)reflected measurement wave intensity})/(\text{second light(short wavelength light)reflected measurement wave intensity})) \quad (4)$$

The discharge unit 5 is a device for causing the surface recombination velocity of the measured sample X to change from the first surface recombination velocity condition to the second surface recombination velocity condition according to the control of the calculation control unit 4, a device for causing the surface of the measured sample X to become at least two or more different surface recombination velocity conditions, and corresponds to an example of the surface recombination velocity changing unit. In this embodiment, the discharge unit 5 is, for example, a corona discharge generating device which generates a corona discharge and applies this corona discharge to the measurement wave irradiated region (light irradiated region) of the measured sample X onto which the measurement wave is irradiated by the measurement wave I/O unit 2, and corresponds to an example of the corona discharge application unit. As the discharge unit 5 is configured, for example, as shown in FIG. 3A, by comprising a first corona wire 51 as a first electrode which is subject to a corona discharge when a high voltage is applied to the vicinity of the opening 22a of the waveguide antenna 22, a second corona wire 52 as second electrode which is subject to a corona discharge when a high voltage is applied to the vicinity of the rear face (rear face region) of the measured sample X facing the measurement wave irradiated region of the measured sample X onto which the measurement wave is irradiated, a power source unit 53 which generates the high voltage for supplying the high voltage to first and second corona wires 51, 52, respectively, and a mounting member 54 for mounting the second corona wire 52 near the rear face region.

The first and second corona wires 51, 52 are, for example, tungsten wire or the like having a wire diameter of 0.1 mm. In FIG. 3B, the waveguide antenna 22 is, for example, an angular tube, a part of the two surfaces of the opening 22a facing each other is cut out, and a predetermined insulator 51a is provided to each of the cutout portions. In addition, the first corona wire 51 is mounted so as to cut across the center of the opening 22a by causing it to cross over the two facing insulators 51a (FIG. 3B shows only one insulator 51a). Moreover, the first corona wire 51 is connected to the power source unit 53 via the connecting wire 51b, and the first corona wire 51 and the waveguide antenna 22 are insulated thereby. The second corona wire 52 is similarly insulated and mounted by the mounting member 54. Moreover, in order to dispose the measured sample X between the first corona wire 51 and the second corona wire 52, a supporting member not shown for supporting the measured sample X is provided. Based on the foregoing configuration, it is possible to apply a corona discharge, which was generated by using the power source unit 53 to apply a predetermined voltage to the electrodes of the first and second corona wires 51, 52 provided in the vicinity of the measured sample X, to the measured sample X.

Figure 4:
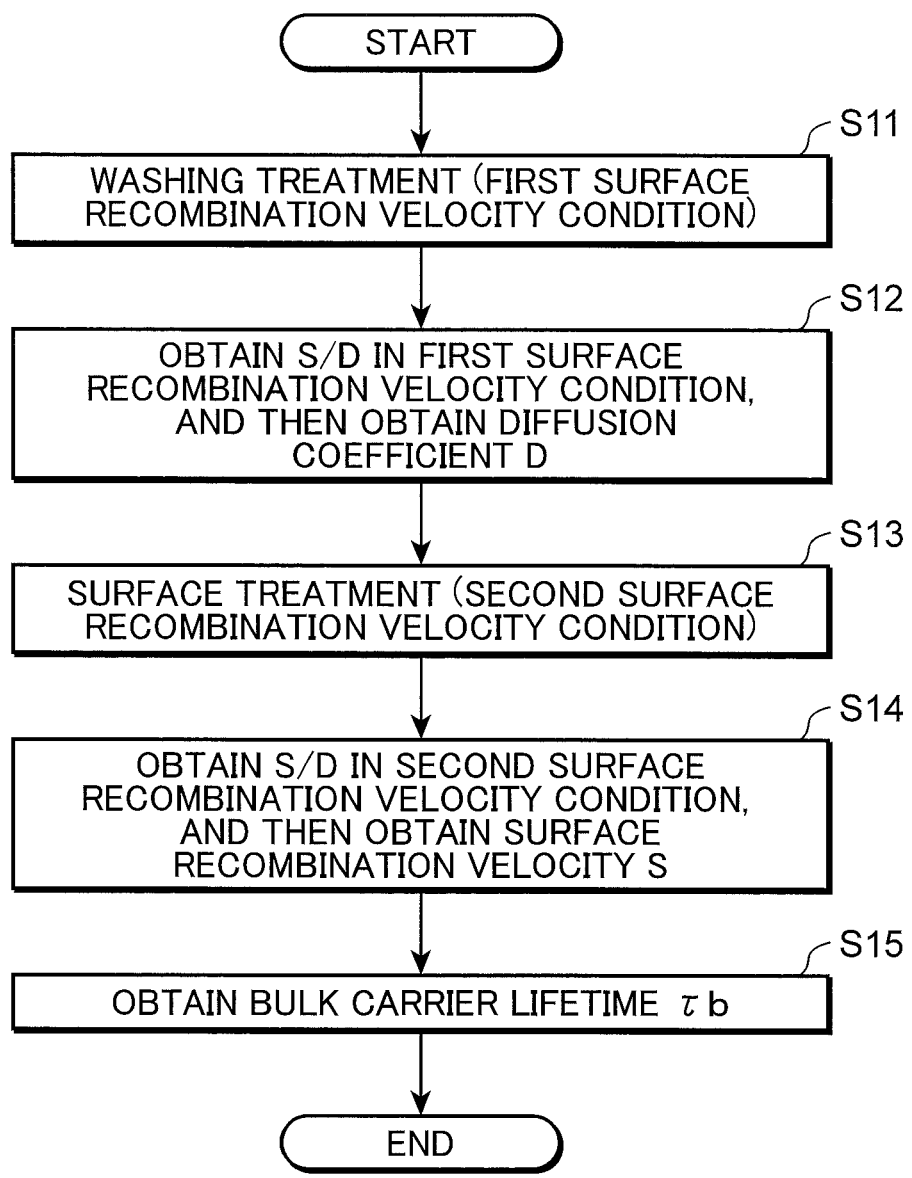
FIG. 4 is a flowchart showing an example of the operation of the semiconductor carrier lifetime measuring apparatus shown in FIG. 3.
Figure 5:
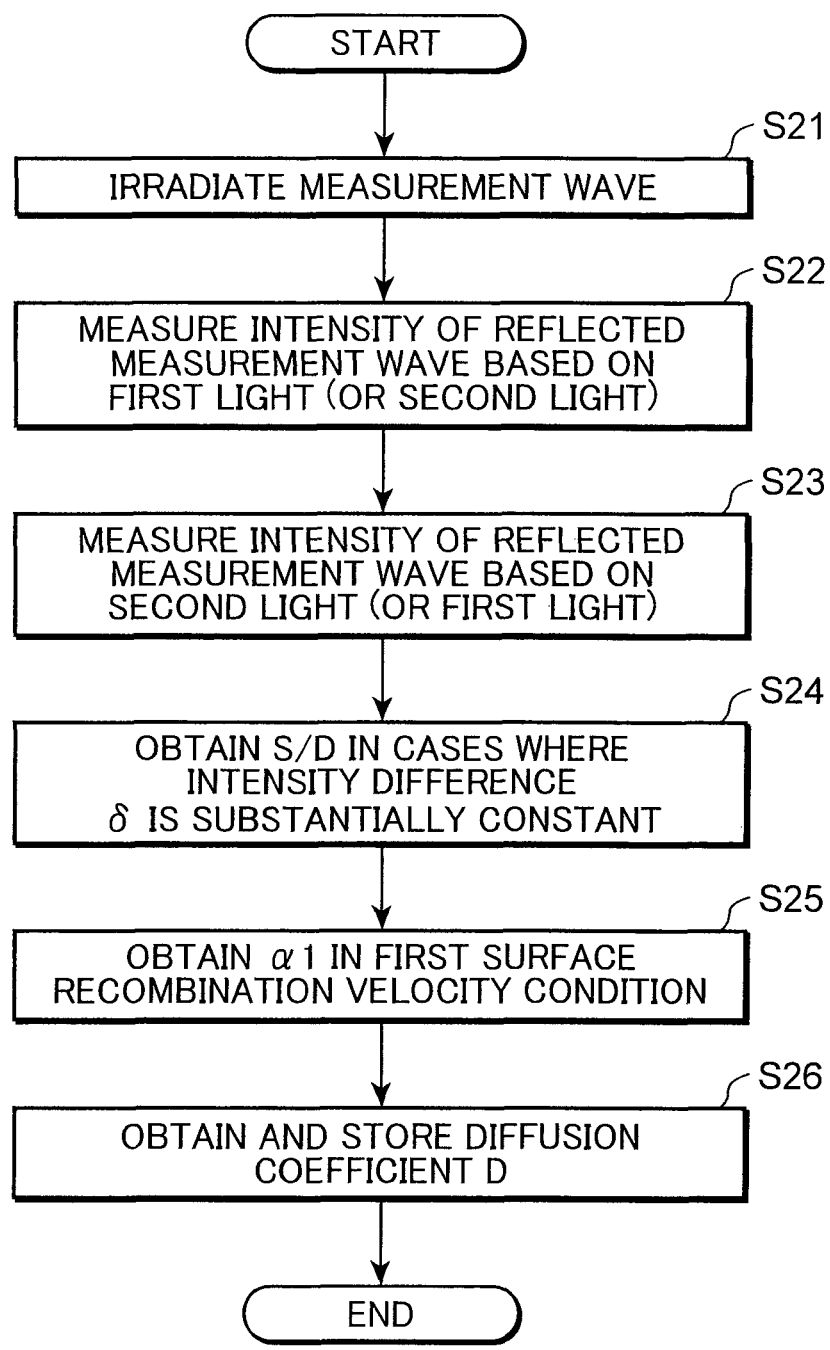
FIG. 5 is a flowchart showing the operation of the semiconductor carrier lifetime measuring apparatus shown in FIG. 3 in cases of obtaining the diffusion coefficient.
Figure 6:
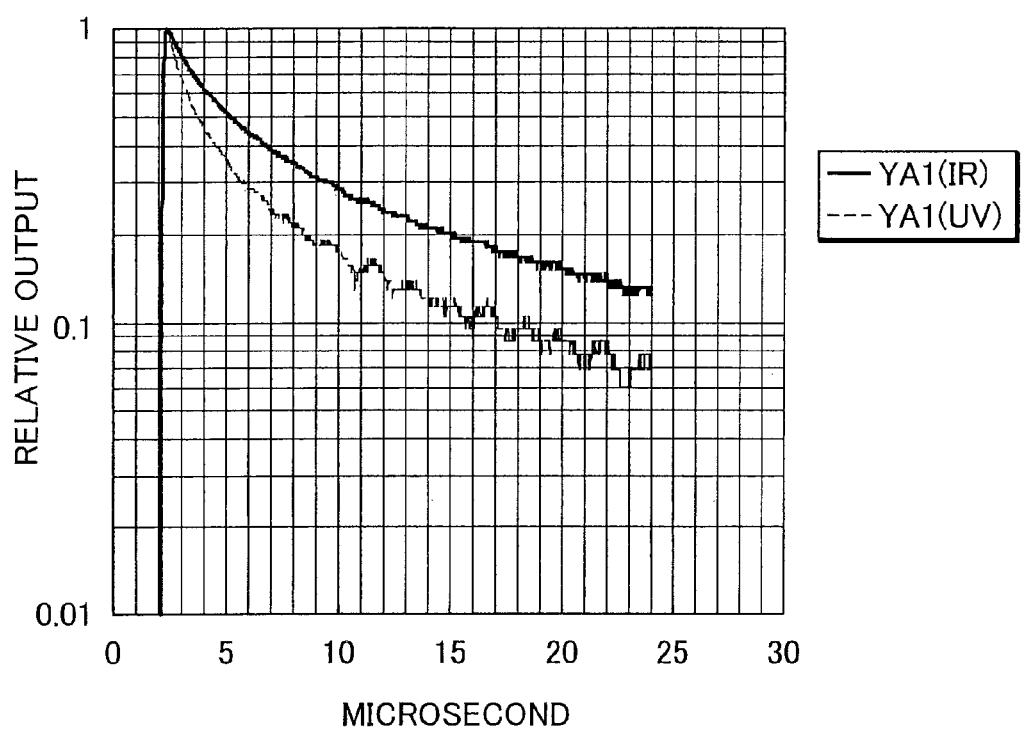
FIG. 6 is a diagram showing the time change of the relative output of the reflected measurement wave regarding each of the two lights having mutually different wavelengths in the analyzed example.
Figure 7:
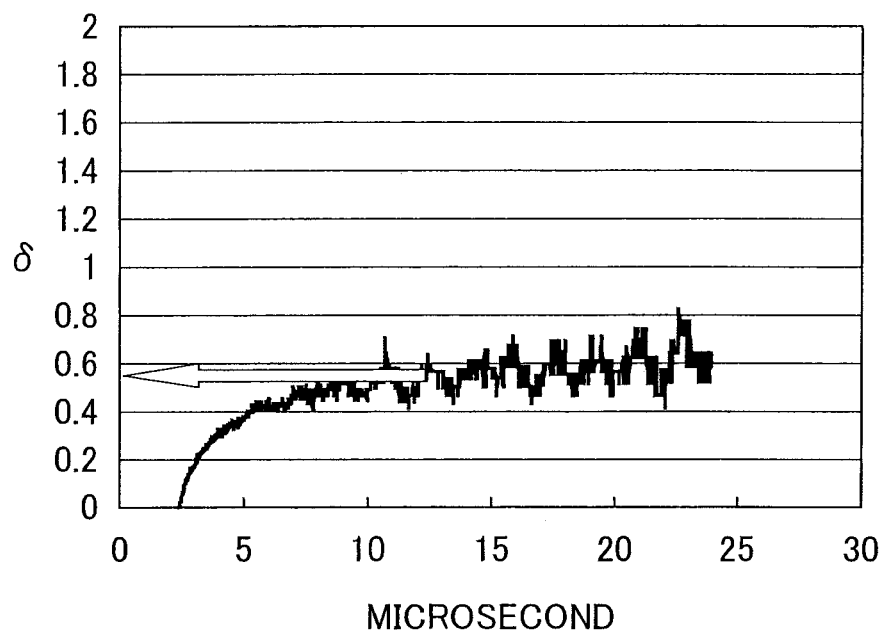
FIG. 7 is a diagram showing the time change of the relative output of the reflected measurement wave regarding each of the two lights having mutually different wavelengths in the analyzed example.
Figure 8:
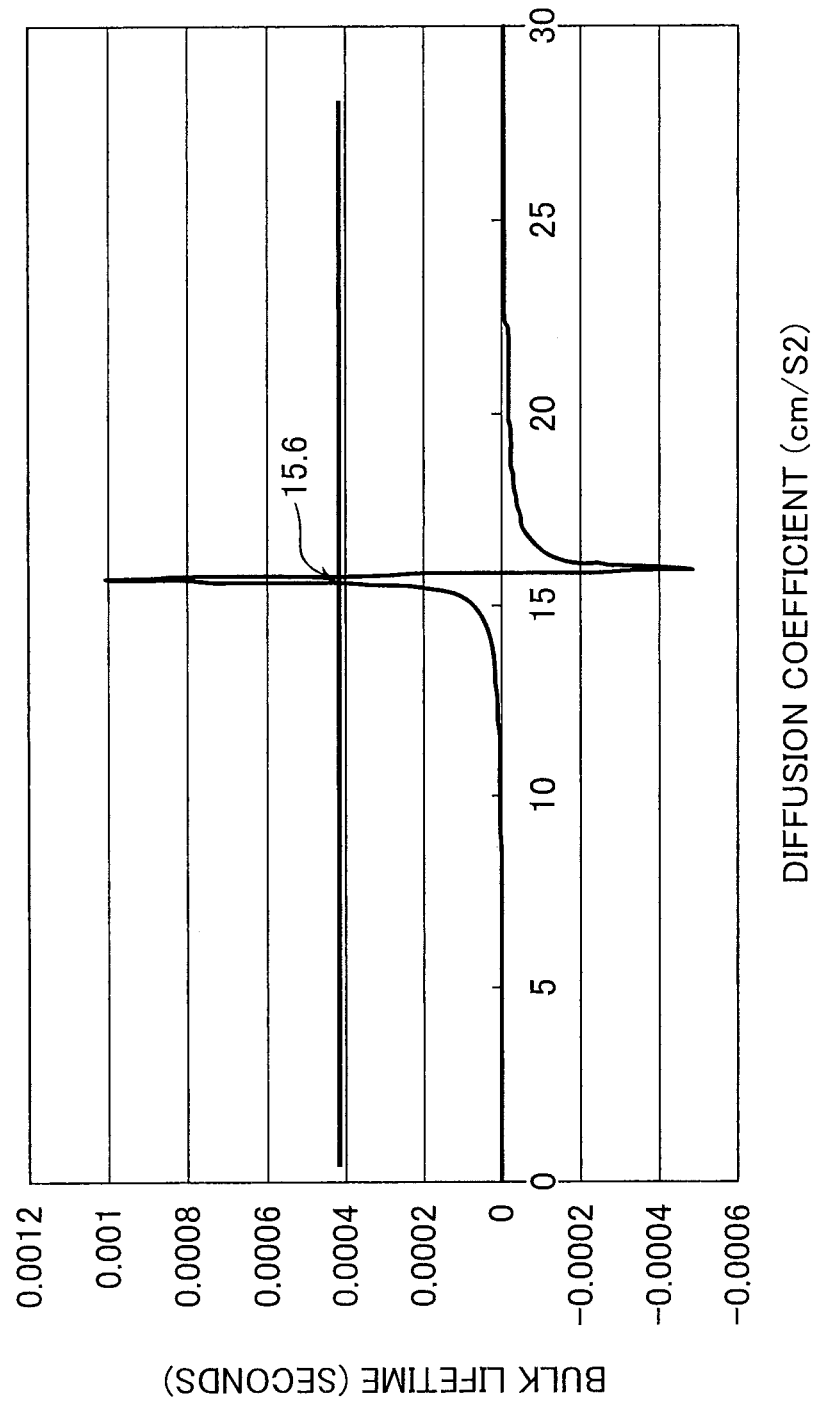
FIG. 8 is a diagram showing the relationship of the diffusion coefficient and the bulk carrier lifetime when S/D=4000.

The semiconductor carrier lifetime measuring apparatus A1 configured as described above measures the bulk carrier lifetime τb of the semiconductor, for example, based on the following operation. FIG. 4 is a flowchart showing an example of operating the semiconductor carrier lifetime measuring apparatus of the first embodiment. FIG. 5 is a flowchart showing the operation of the semiconductor carrier lifetime measuring apparatus in cases of obtaining the diffusion coefficient. FIG. 6 is a diagram showing the time change of the relative output of the reflected measurement wave regarding each of the two lights having mutually different wavelengths in the analyzed example. The horizontal axis of FIG. 6 is the elapsed time represented in microseconds, and its vertical axis is the relative output (reflected wave relative intensity of the measurement wave). The intensity of the reflected measurement wave in a case of irradiating light having a wavelength of an infrared region is shown with a bold line (YA1 (IR)), and the intensity of the reflected measurement wave in a case of irradiating light having a wavelength of an ultraviolet region is shown with a bold line (YA1 (UR)). FIG. 7 is a diagram showing the time change of the relative output of the reflected measurement wave regarding each of the two lights having mutually different wavelengths in the analyzed example. The horizontal axis of FIG. 7 is the same as the horizontal axis of FIG. 6, and its vertical axis is the relative output difference δ of the reflected wave of the measurement wave in each light. FIG. 8 is a diagram showing the relationship of the diffusion coefficient and the bulk carrier lifetime when S/D=4000. The horizontal axis of FIG. 8 is the diffusion coefficient D represented in cm/s$^2$ units, and its vertical axis is the bulk carrier lifetime τb represented in s (second) units.

In FIG. 4, foremost, contamination and surface damage on the surface of the semiconductor wafer to be measured are foremost removed in advance via, for instance, so-called chemical etching (washing treatment), whereby achieved is a state where a natural oxide film has been applied (S11). This state in which the natural oxide film has been applied is the first surface recombination velocity condition. In addition, the semiconductor wafer that was subject to the foregoing washing treatment is thereafter placed, as the measured sample X, on the supporting member, and is set at a predetermined measurement position that is sandwiched between the first corona wire 51 and the second corona wire 52.

Subsequently, S/D in the case where the measured sample X is in the first surface recombination velocity condition is obtained, and the diffusion coefficient D is obtained based on the obtained S/D (S12).

More specifically, the measurement wave is irradiated onto the measurement wave irradiated region (light irradiated region) of the measured sample X by the measurement wave I/O unit 2 according to the control of the calculation control unit 4, the measurement wave that was reflected by the measured sample X is detected by the detection unit 3, and the detection results are output from the detection unit 3 to the calculation control unit 4. Even more specifically, the measurement wave generation unit 21 generates the measurement wave according to the control of the calculation control unit 4, and the generated measurement wave enters the first terminal of the circulator 25. The measurement wave that entered from the first terminal is output from the second terminal of the circulator 25, enters the waveguide 24, and is propagated within the waveguide 24. The electric field and magnetic field of the measurement wave propagating in the waveguide 24 are adjusted via the E-H tuner 23 provided midway, and the measurement wave is emitted from the opening 22a of the waveguide 22 toward the measurement wave irradiated region so as to irradiate the measurement wave irradiated region of the measured sample X. In addition, the measurement wave (reflected measurement wave) that was reflected by the measured sample X enters from the opening 22a of the waveguide antenna 22, and is received by the waveguide antenna 22. The reflected measurement wave propagates in the waveguide 24 via the E-H tuner 23, and enters the second terminal of the circulator 25. The reflected measurement wave that entered from the second terminal is output from the third terminal of the circulator 25, enters the detection unit 3, and its intensity is detected by the measurement wave detection unit 31 of the detection unit 3. The detected intensity of the reflected measurement wave is output from the measurement wave detection unit 31 of the detection unit 3 to the calculation unit 41 of the calculation control unit 4.

Meanwhile, the first and second light are irradiated onto the light irradiated region (measurement wave irradiated region) of the measured sample X based on time-division by the light irradiation unit 1 according to the control of the calculation control unit 4. Even more specifically, foremost, the first light source unit 11-1 outputs the first light of the pulsed laser beam according to the control of the calculation control unit 4, the light path of the output first light is bent by the first mirror 12-1, the first light enters the opening 22b of the waveguide antenna 22 and propagates within the waveguide antenna 22, and is output from the opening 22a of the waveguide antenna 22 toward the light irradiated region so as to irradiate the light irradiated region of the measured sample X. Moreover, secondly, the second light source unit 11-2 outputs the second light of the pulsed laser beam according to the control of the calculation control unit 4, the light path of the output second light is bent by the second mirror 12-2, the second light enters the opening 22b of the waveguide antenna 22 and propagates within the waveguide antenna 22, and is output from the opening 22a of the waveguide antenna 22 toward the light irradiated region so as to irradiate the light irradiated region of the measured sample X. Note that the order of irradiating the first light and the second light may be the opposite to the above.

Therefore, if the measurement wave is irradiated onto the measured sample X while the first light is being irradiated on to the measured sample X as described above, the intensity change of the reflected measurement wave caused by the first light is introduced into the calculation unit 41 via the measurement wave detection unit 31. Moreover, if the measurement wave is irradiated onto the measured sample X while the second light is being irradiated onto the measured sample X, the intensity change of the reflected measurement wave caused by the second light is introduced into the calculation unit 41 via the measurement wave detection unit 31. Normally, as shown in FIG. 5, the measurement wave is irradiated onto the measured sample X (S21), the intensity change of the reflected measurement wave immediately after the irradiation (immediately after the extinction) of the first light (or second light) of the pulsed laser beam is measured by irradiating the first light (or second light) of the pulsed laser beam while irradiating the measurement wave onto the measured sample X (S22) and, additionally, the intensity change of the reflected measurement wave immediately after the irradiation (immediately after the extinction) of the second light (or first light) of the pulsed laser beam is measured by irradiating the second light (or first light) of the pulsed laser beam while irradiating the measurement wave onto the measured sample X (S23). In addition, since the wavelengths of the first and second light are mutually different, their lengths of penetration relative to the measured sample X will also be mutually different, and, consequently, it is possible to obtain the intensity of the respective measurement waves based on the irradiation of the first and second light having mutually different lengths of penetration.

For example, as shown in FIG. 6, the intensity of the reflected measurement wave decreases with the lapse of time, and eventually becomes substantially constant when the carrier enters a state of thermal equilibrium. In addition, during the course that the reflected measurement wave intensity decreases, the decrease ratio (rate of decrease, amount of decrease per unit time) is relatively large initially, and decreases with the lapse of time. Moreover, the temporal intensity change of the reflected measurement wave caused by the infrared laser beam (IR) of the first light is smaller than the temporal intensity change of the reflected measurement wave caused by the ultraviolet laser beam (UV) of the second light. In addition, as shown in FIG. 7, the difference δ between the intensity of the reflected measurement wave caused by the infrared laser beam (IR) of the first light and the intensity of the reflected measurement wave caused by the ultraviolet laser beam (UV) of the second light decreases with the lapse of time, and eventually becomes substantially constant. Note that FIG. 6 and FIG. 7 are analyzed examples in cases where the measured sample X is a semiconductor wafer that was subject to hydrofluoric acid cleansing, and the surface recombination velocity S is 9000 cm/s and the bulk carrier lifetime τb is 79 μs.

Subsequently, the first condition calculation unit 411 of the calculation unit 41 obtains the δ value based on the output of the measurement wave detection unit 31, obtains a value in which the δ value became substantially constant as described above, and, by referring to the δ-S/D table of the δ-S/D table storage unit 415, obtains S/D corresponding to the value in which the δ value became substantially constant (S24).

Subsequently, the first condition calculation unit 411 of the calculation unit 41 obtains a1 in the first surface recombination condition by using the obtained S/D in Formula 2 (S25).

Subsequently, the first condition calculation unit 411 of the calculation unit 41 obtains the diffusion coefficient D by evaluating the bulk carrier lifetime τb relative to the diffusion coefficient in the measured sample X by using Formula 5, which is a modification of Formula 1, and stores the obtained diffusion coefficient D in the diffusion coefficient storage unit 414 (S26). In this processing, a in Formula 5 is α1.

$$\tau b = 1(1/\tau 1) - \alpha^2 \times D) \quad (5)$$

When the bulk carrier lifetime τb is a relatively large value such as 100 μs, preferably 1000 μs (=1 ms), the diffusion coefficient D becomes a value that coincides with the peak value of Formula 5.

For example, when S/D=4000 and the measurement result τ1=4 μs, the bulk carrier lifetime τb based on Formula 5 becomes the graph shown in FIG. 8 when the diffusion coefficient D is calculated across a predetermined range including the peak; for instance, across a range of 0 to 30, and the bulk carrier lifetime τb based on Formula 5 will have a peak at one point. The value at this peak (approximately 15.6 in the example of FIG. 8) will be the diffusion coefficient D.

Based on the respective processes described above, S/D in cases where the measured sample X is in the first surface recombination velocity condition is obtained, and the diffusion coefficient D is obtained based on the obtained S/D.

Returning to FIG. 4, subsequently, surface treatment of the measured sample X is performed based on the obtained diffusion coefficient D (approximately 15.6 in the example of FIG. 8) (S13). Preferably, this surface treatment is, for instance, corona discharge treatment, oxidation treatment, passivation treatment that is performed by depositing silicon nitride, amorphous silicon and alumina film, and so on. In this embodiment, since surface treatment can be temporarily performed only for the time that is required for the measurement and then returned to its original state after the measurement, corona discharge treatment is adopted as the surface treatment of the measured sample X. More specifically, the power source unit 53 applies a high voltage of mutually different polarities to the first and second corona wires 51, 52 according to the control of the calculation control unit 4. Consequently, a corona discharge is provided from the first and second corona wires 51, 52, respectively, to both main surfaces of the measured sample X, whereby surface treatment is performed.

Subsequently, S/D in cases where the measured sample X is in the second surface recombination velocity condition is obtained, and the surface recombination velocity S is obtained based on the obtained S/D (S14).

More specifically, as a result of performing the same processes as the respective processes of processing S21 to processing S23, which were explained with reference to FIG. 5, while applying a high voltage to the first and second corona wires 51, 52 by using the power source unit 53, the intensity change of the reflected measurement wave caused by the first light is detected by the measurement wave detection unit 31, and, in addition, the intensity change of the reflected measurement wave caused by the second light is detected by the measurement wave detection unit 31, and the intensity changes of the respective reflected measurement waves are incorporated into the calculation unit 41.

Subsequently, based on processing that is the same as processing S24 explained with reference to FIG. 5, the second condition calculation unit 412 of the calculation unit 41 obtains the δ value based on the output of the measurement wave detection unit 31, obtains a value in which the δ value becomes substantially constant, and, by referring to the δ-S/D table of the δ-S/D table storage unit 415, obtains S/D corresponding to the value in which the δ value becomes substantially constant.

Subsequently, the first condition calculation unit 412 of the calculation unit 41 obtains the surface recombination velocity S by multiplying the obtained S/D by the diffusion coefficient D obtained as described above.

Based on the respective processes described above, S/D in cases where the measured sample X is in the second surface recombination velocity condition is obtained, and the surface recombination velocity S is obtained based on the obtained S/D.

Subsequently, the lifetime calculation unit 413 of the calculation unit 41 obtains the bulk carrier lifetime τb by using Formula 1 and Formula 2 based on the obtained surface recombination velocity S (S15).

In addition, the semiconductor carrier lifetime measuring apparatus A1 outputs the obtained bulk carrier lifetime τb to, for example, an output device not shown such as a display device or a printing device.

Note that, for the second measurement onward, by using the diffusion coefficient D that is stored in the diffusion coefficient storage unit 414, processing S11 and processing S12 can be omitted, and the measurement can be started from processing S13.

Accordingly, the semiconductor carrier lifetime measuring apparatus A1 of this embodiment can measure the carrier lifetime in the production line since it only needs to obtain the first difference of the temporal relative change of the reflected measurement wave in the first surface recombination velocity condition and the second difference of the temporal relative change of the reflected measurement wave in the second surface recombination velocity condition. Moreover, there is no need to perform pretreatment in advance as with conventional technology, and it is possible to more accurately measure the carrier lifetime in comparison to conventional technology. In addition, since it is only necessary to obtain the first difference and the second difference as described above, there is no need to assume the value of the diffusion coefficient in the semiconductor to be measured, and the carrier lifetime can be measured more accurately in comparison to conventional technology.

Generally speaking, when light is irradiated onto a semiconductor, the light (incident light) will penetrate the semiconductor, but the length of penetration will depend on the wavelength of the incident light. With the semiconductor carrier lifetime measuring apparatus A1 of this embodiment, as the light to be irradiated onto the semiconductor as the measured sample X, used are a first light having a wavelength of an infrared region and a second light having a wavelength of an ultraviolet region, or a first light having a wavelength of an infrared region and a third light having a wavelength of a visible region. Thus, since the wavelength difference of these lights is great, the difference in their lengths of penetration will also increase. It is thereby possible to cause the ratio of influence caused by the surface recombination contained in the reflected measurement wave based on the respective lights, to differ considerably. Accordingly, the semiconductor carrier lifetime measuring apparatus A1 of this embodiment can more accurately measure the carrier lifetime in comparison to conventional technology.

Moreover, the semiconductor carrier lifetime measuring apparatus A1 of this embodiment comprises a discharge unit 5 which applies a corona discharge to the measurement wave irradiated region of the measured sample X as an example of the surface recombination velocity condition changing unit which causes the surface recombination velocity condition of the measured sample X to change from the first surface recombination velocity condition to the second surface recombination velocity condition. Thus, the semiconductor carrier lifetime measuring apparatus A1 of this embodiment can change the surface recombination velocity condition in the measured sample X from its first condition to its second condition by using the discharge unit 5 as an example of the surface recombination velocity condition changing unit, and realize the second recombination velocity condition with the corona discharge. Moreover, since the second surface recombination velocity condition is realized by the corona discharge, the physical-chemical behavior in the measured sample X can be returned to its original state by ending the application of the corona discharge.

Under normal circumstances, before a semiconductor wafer is used, a natural oxide film is formed on its surface through washing treatment for removing contamination such as fouling. With the semiconductor carrier lifetime measuring apparatus A1 of this embodiment, since the natural oxide film that was exposed by the washing treatment becomes the first surface recombination velocity condition, the treatment for realizing the first surface recombination velocity condition can double as the foregoing washing treatment, and the number of man-hours can be reduced.

The measurement error in the semiconductor carrier lifetime measuring apparatus A1 of this embodiment is now examined.

The difference $\delta$ of the temporal relative change is the same as obtaining the ratio of S/D, and in a state where the diffusion coefficient D is unknown, the surface recombination velocity S is left undecided, and the bulk carrier lifetime $\tau b$ is also left undecided. In particular, for instance, with a semiconductor wafer that is not subject to so-called surface treatment via washing treatment such as chemical etching, normally, the measured (observed) surface recombination velocity S is approximately 10000 cm/s, and, therefore, the bulk lifetime $\tau b$ will be roughly several microseconds. Accordingly, in the foregoing case, even if the diffusion coefficient D is accurately obtained, estimation of the primary mode lifetime $\tau$ is demand of precision of 0.01%, and this is not realistic. In addition, it is anticipated that the diffusion coefficient D will differ for each wafer, even in cases where the wafers are separated from the same ingot of the semiconductor.

Meanwhile, with the semiconductor carrier lifetime measuring apparatus A1 of this embodiment, the diffusion coefficient D is foremost obtained by measuring the measured sample X in a state of the natural oxide film based on the washing treatment, surface treatment (corona discharge) for reducing the surface recombination velocity S is thereafter performed, and, in this state, the measured sample X is measured once again. The measurement accuracy (deviation from the true value; %) of the primary mode lifetime T in the foregoing measurement is as shown in Table 1 to Table 3. For example, in order to obtain the bulk lifetime $\tau b$ with an accuracy of roughly 10%, the measurement accuracy of the primary mode lifetime only needs to be roughly 1%. Note that Table 1 shows a case where the measurement accuracy of the primary mode lifetime is ±10%, Table 2 shows a case where the measurement accuracy of the primary mode lifetime is ±1%, and Table 3 shows a case where the measurement accuracy of the primary mode lifetime is ±0.1%.

TABLE 1

Primary mode lifetime measurement accuracy: ±10%

| Bulk lifetime | | S = 10 | S = 100 | S = 1000 | S = 10000 |
|---|---|---|---|---|---|
| 1000 | 10% | 22.18308 | 6178.499 | NG | NG |
| | −10% | −18.1777 | −54.6269 | −90.581 | −97.4696 |
| 500 | 10% | 15.76585 | 116.3388 | NG | NG |
| | −10% | −14.2875 | −39.6572 | −82.9151 | −95.0725 |
| 100 | 10% | 11.10475 | 22.00166 | 652.6865 | NG |
| | −10% | −10.8931 | −18.05 | −51.4255 | −79.7967 |

TABLE 2

Primary mode lifetime measurement accuracy: ±1%

| Bulk lifetime | | S = 10 | S = 100 | S = 1000 | S = 10000 |
|---|---|---|---|---|---|
| 1000 | 1% | 2.006402 | 11.94409 | 499.7719 | NG |
| | −1% | −1.98987 | −9.90497 | −47.2022 | −77.9924 |
| 500 | 1% | 1.495633 | 6.224118 | 75.82707 | NG |
| | −1% | −1.50229 | −5.63535 | −30.661 | −63.7381 |
| 100 | 1% | 1.096924 | 2.010034 | 10.4852 | 53.64586 |
| | −1% | −1.10264 | −1.95681 | −8.74043 | −26.5461 |

TABLE 3

Primary mode lifetime measurement accuracy: ±0.1%

| Bulk lifetime | | S = 10 | S = 100 | S = 1000 | S = 10000 |
|---|---|---|---|---|---|
| 1000 | 0.1% | 0.188317 | 1.03888 | 6.898329 | 42.77855 |
| | −0.1% | −0.21127 | −1.12514 | −9.76196 | −28.2077 |
| 500 | 0.1% | 0.139156 | 0.597388 | 4.441503 | 20.39063 |
| | −0.1% | −0.16063 | −0.58572 | −4.28883 | −15.0997 |

TABLE 3-continued

| Primary mode lifetime measurement accuracy: ±0.1% | | | | |
|---|---|---|---|---|
| Bulk lifetime | S = 10 | S = 100 | S = 1000 | S = 10000 |
| 100 | 0.1% | 0.106033 | 0.205633 | 1.014152 | 3.403913 |
| | −0.1% | −0.11392 | −0.19101 | −0.89454 | −3.6729 |

Note that, in the foregoing embodiment, in order to more accurately measure the actual characteristics of the semiconductor wafer for use in photovoltaic cells (PV semiconductor wafer) in a state where light is being irradiated to generate power, the semiconductor carrier lifetime measuring apparatus A1 can also be configured, as shown with the broken line in FIG. 3, by further comprising a power-generating irradiation unit 6 which irradiates a power-generating light onto the measured sample X. The power-generating irradiation unit 6 is configured, for example, by comprising a third light source unit 61 which emits a power-generating light (bias light) having a predetermined spectral distribution which is pre-set according to the control of the calculation control unit 4, and a light-guiding member 62 such as an optical fiber which guides the bias light emitted from the third light source unit 61 toward the light irradiated region (measurement wave irradiated region) of the measured sample X, and the bias light that was emitted from the third light source unit 61 is irradiated on the light irradiated region of the measured sample X via the light-guiding member 62. Consequently, the PV semiconductor wafer as the measured sample X is biased by the power-generating light. The predetermined spectral distribution is arbitrarily decided according to the photoexcited carrier or the like of the PV semiconductor wafer to be measured. From the perspective of more accurately measuring the carrier lifetime of the PV semiconductor wafer using solar light, the third light source unit 61 may be an illuminating device which illuminates light that emulates the same optical spectrum and irradiance as solar light. Moreover, from the foregoing perspective, the third light source unit 61 preferably emits light corresponding to 1 SUN, and more preferably emits light having a simulated solar light spectrum. In the measurement of the bulk carrier lifetime τb, each of the foregoing processes is executed while the power-generating irradiation unit 6 irradiates the bias light onto the measured sample X. As a result of further comprising this kind of power-generating irradiation unit 6, the semiconductor carrier lifetime measuring apparatus A1 can more accurately measure the actual characteristics of the PV semiconductor wafer in a state where light is being irradiated for generating power. In addition, since the specific resistance of the PV semiconductor wafer is varied across a relatively broad range, a diffusion coefficient in the light-irradiated state is required since light is irradiated onto the PV semiconductor wafer upon evaluating the actual power-generating characteristics, but it is difficult to estimate the diffusion coefficient of the PV semiconductor wafer. However, since the semiconductor carrier lifetime measuring apparatus A1 of this embodiment operates as described above, it can more accurately measure the bulk carrier lifetime τb in comparison to conventional technology.

Moreover, in the foregoing embodiment, although the detection unit 3 detects the reflected wave of the measurement wave that was irradiated onto the measured sample X, it may also be configured to detect the transmitted wave of the measurement wave that was irradiated onto the measured sample X. For example, the detection unit 3 is configured by providing a waveguide which guides the transmitted wave of the measurement wave, so that it does not interfere with the second corona wire 52, in the vicinity of the rear face (rear face region) of the measured sample facing the measurement wave irradiated region of the measured sample X onto which the measurement wave is irradiated, guiding the transmitted wave of the measurement wave to the measurement wave detection unit 31 of the detection unit 3 by using the foregoing waveguide, and thereby detecting the intensity of the transmitted wave of the measurement wave. Even with this kind of configuration, the semiconductor carrier lifetime measuring apparatus A1 can measure the bulk carrier lifetime τb based on each of the similar processes of measuring the reflected wave of the measurement wave.

Another embodiment is now explained.

(Second Embodiment)

Figure 9:
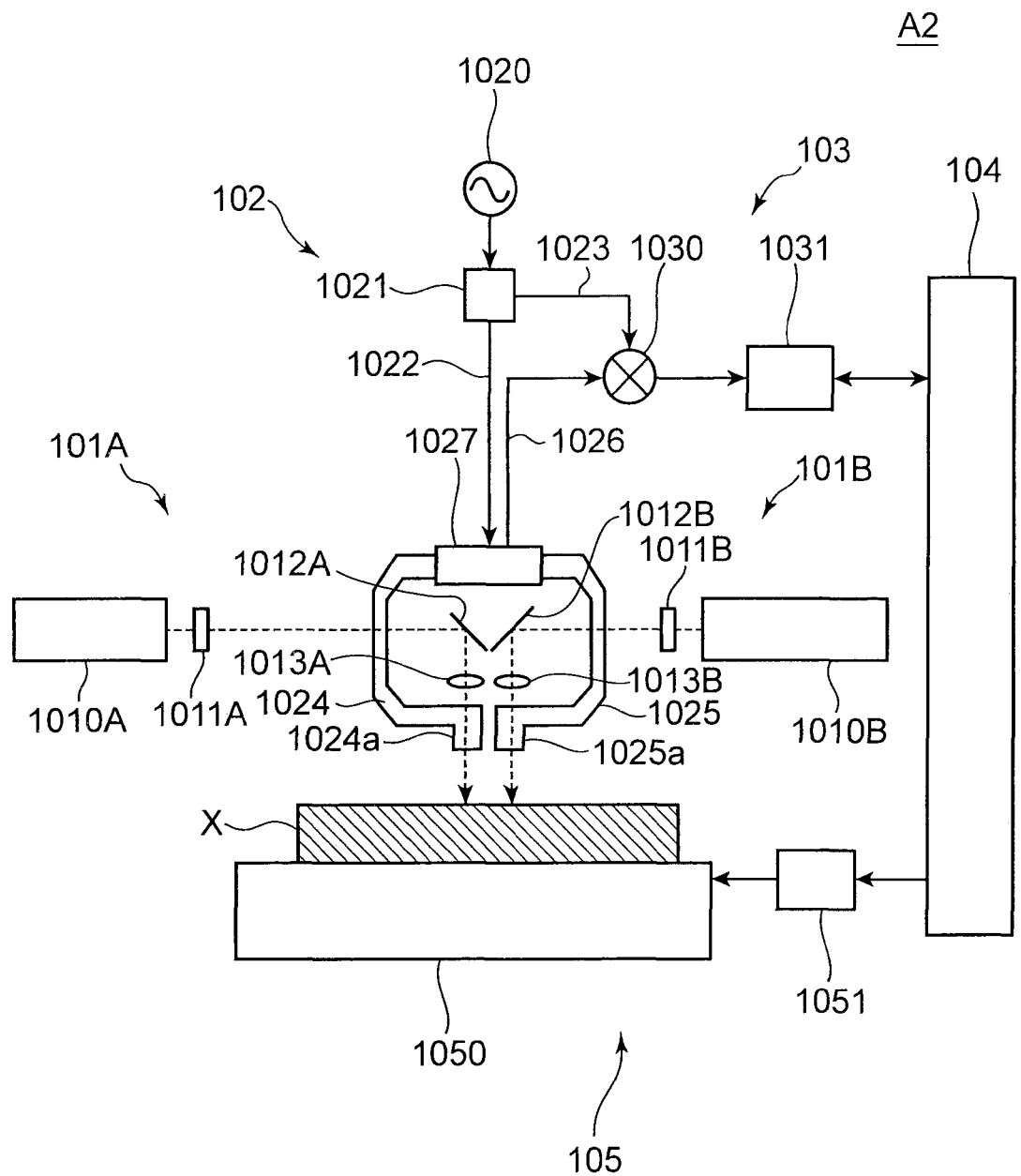
FIG. 9 is a diagram showing the configuration of the semiconductor carrier lifetime measuring apparatus in the second embodiment.
Figure 10:
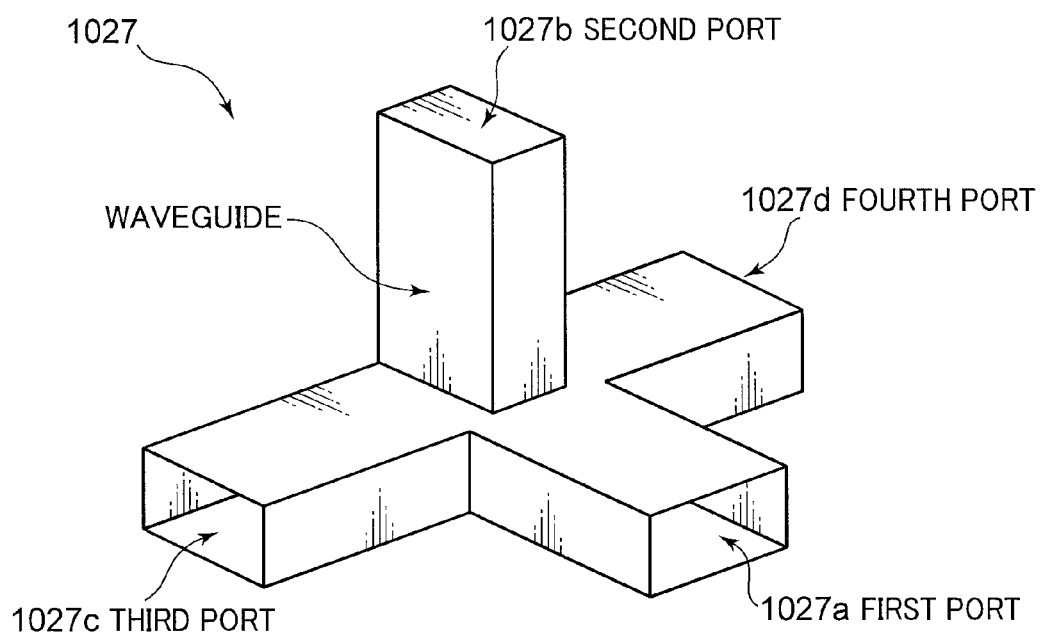
FIG. 10 is a perspective view showing the configuration of the magic T that is used in the semiconductor carrier lifetime measuring apparatus shown in FIG. 9.
Figure 11:
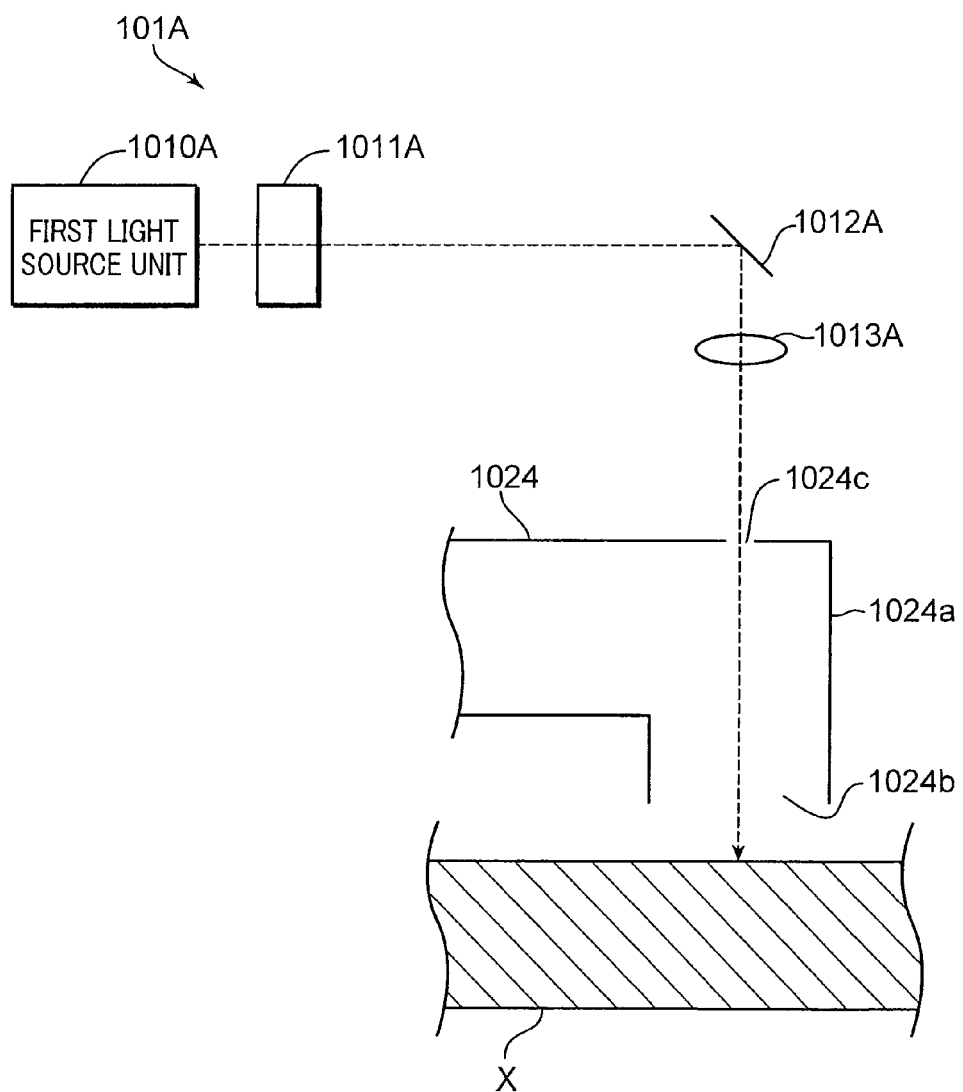
FIG. 11 is a diagram showing the configuration of the portion relating to the irradiation of light in the semiconductor carrier lifetime measuring apparatus shown in FIG. 9.

FIG. 9 is a diagram showing the configuration of the semiconductor carrier lifetime measuring apparatus in the second embodiment. FIG. 10 is a perspective view showing the configuration of the magic T that is used in the semiconductor carrier lifetime measuring apparatus in the second embodiment. FIG. 11 is a diagram showing the configuration of the portion relating to the irradiation of light in the semiconductor carrier lifetime measuring apparatus of the second embodiment.

The semiconductor carrier lifetime measuring apparatus A2 of the second embodiment is a device which measures the carrier lifetime of the semiconductor based on the so-called microwave photoconductive decay method, and is a device which irradiates at least two types of light having mutually different wavelengths onto mutually different first and second regions in the semiconductor so as to generate excess carriers, irradiates a measurement wave such as a microwave in order to detect the extinction process of the excess carriers, directly generates the difference (difference measurement wave) between the thus obtained reflected wave or transmitted wave of the measurement wave from the first region and the reflected wave or transmitted wave of the measurement wave from the second region, measures the directly-generated difference (difference measurement wave) itself with a detector by using the entire dynamic range thereof, and obtains the carrier lifetime of the semiconductor based on the detection results.

This kind of semiconductor carrier lifetime measuring apparatus A2 of the second embodiment is configured, for example, as shown in FIG. 9, an light irradiation unit 101 (101A, 101B), a measurement wave I/O unit 102, a detection unit 103, and a calculation control unit 104, and further comprises a move part 105 for moving the measurement location.

The light irradiation unit 101 is a device for emitting at least two types of light having mutually different wavelengths onto mutually different first and second regions in a semiconductor wafer (measured sample) X, such as a silicon wafer, to be measured, in order to cause the lengths of penetration to be mutually different. With the semiconductor carrier lifetime measuring apparatus A2 of this embodiment, the light irradiation unit 101 is configured, as shown in FIG. 9, for example, by comprising a first light irradiation unit 101A and a second light irradiation unit 101B so as to irradiate the first light of the first wavelength onto the first region of the measured sample X, and irradiating the second light of the second wavelength, which is different from the first wavelength, to a second region that is different from the first region in the measured sample X.

These first and second regions are used for prescribing the measurement range that to be measured by the semiconductor carrier lifetime measuring apparatus A2, and the distance between the center position of the first region (for example, barycentric position of the light intensity of the first light that is irradiated onto the first region) and the center position of the second region (for example, barycentric position of the light intensity of the second light that is irradiated onto the second region) is used for prescribing the spatial resolution of the semiconductor carrier lifetime measuring apparatus A2. Accordingly, the first and second regions are set to be adjacent to each other, and, although the distance is a predetermined length that is arbitrarily set based on the specification or the like concerning the spatial resolution of the semiconductor carrier lifetime measuring apparatus A2, it is desirably short so that the first and second regions become close in order to cause the spatial resolution to be high resolution. Since the distance is also restricted by the size of the first waveguide antenna 1024a and the second waveguide antenna 1025a described later in the measurement wave I/O unit 102, it is, for example, several millimeters.

The first light irradiation unit 101A is configured by comprising a first light source unit 1010A which outputs a first light of a first wavelength according to the control of the calculation control unit 104, a first mirror 1012A which directs the first light that was output from the first light source unit 1010A toward the measured sample X and bends its light path approximately 90 degrees, and a first lens 1013A which applies a lens effect to the first light that was reflected by the first mirror 1012A for adjusting the light irradiation diameter and the light intensity distribution on the surface of the measured sample X, and the first light that is subject to the lens effect by the first lens 1013A is irradiated onto the first region of the measured sample X via the third waveguide 1024 as described later.

Similarly, the second light irradiation unit 101B is configured by comprising a second light source unit 1010B which outputs a second light of a second wavelength according to the control of the calculation control unit 104, a second mirror 1012B which directs the second light that was output from the second light source unit 1010B toward the measured sample X and bends its light path approximately 90 degrees, and a second lens 1013B which applies a lens effect to the second light that was reflected by the second mirror 1012B, and the second light that is subject to the lens effect by the second lens 1013B is irradiated onto the second region of the measured sample X via the fourth waveguide 1025 as described later.

The first and second light source units 1010A, 1010B may be, for instance, a light source device or the like comprising a lamp and a wavelength filter, but in this embodiment, they are configured by comprising a laser beam source device of, for instance, a semiconductor laser or a YAG laser, which emits laser beams and is able to obtain a relatively large output. The first light and the second light are monochromatic light, and preferably their wavelength difference is large (of a wider interval) so as to generate a greater difference in the length of penetration (difference in the length of penetration of a wider interval), and, for instance, the first light source unit 1010A is a device which emits a laser beam of a predetermined wavelength in an infrared region; that is, an infrared laser beam (IR laser beam), and the second light source unit 1010B is a device which emits a laser beam of a predetermined wavelength in an ultraviolet region; that is an ultraviolet laser beam (UV laser beam). Note that one of either the first or second light source units 1010A, 1010B may also be a device which emits a laser beam of a predetermined wavelength in a visible region; that is, a visible laser beam. The respective wavelengths of the first and second light source units 1010A, 1010B are arbitrarily selected, for example, according to the type of the measured sample X. For example, if the measured sample X is a silicon wafer, in addition to the perspectives described above, from the perspective of efficiency of photo-excitation and cost reduction of the light source 1010 (1010A, 1010B), the respective wavelengths of the first and second light source units 1010A, 1010B are preferably a combination of 904 nm and 349 nm, or a combination of 904 nm and 523 nm. Since the first and second light generate carriers (electrons and holes) in the measured sample X based on photo-excitation as a result of being irradiated onto the measured sample X, and since the semiconductor carrier lifetime measuring apparatus A2 is an apparatus for measuring the lifetime (carrier lifetime) of the generated carriers, the first and second light preferably shift from a non-lit state to a lit-state in a stepwise manner, and, in this embodiment, for example, pulsed light, and more specifically, a pulsed laser beam, is used.

In addition, with the light irradiation unit 101 of the semiconductor carrier lifetime measuring apparatus A2 of this embodiment, the first light irradiation unit 101A further comprises a first light intensity regulator 1011A and the second light irradiation unit 101B further comprises second light intensity regulator 1011B so that the initial first and second excess carrier mass that are generated when the at least two types of light having mutually different wavelengths are irradiated onto the first and second regions in the measured sample X, respectively, become mutually equal.

The first light intensity regulator 1011A is configured, for example, by comprising an optical attenuator which attenuates the light intensity of the entering light and outputs such light, and, in the example shown in FIG. 9, is disposed (inserted) in the light path between the first light source unit 1010A and the first mirror 1012A in the light path from the first light source unit 1010A to the first region surface of the measured sample X. Similarly, the second light intensity regulator 1011B is configured, for example, by comprising an optical attenuator and, in the example shown in FIG. 9, is disposed (inserted) in the light path between the second light source unit 1010B and the second mirror 1012B in the light path from the second light source unit 1010B to the second region surface of the measured sample X.

The measurement wave I/O unit 102 is a device which irradiates a predetermined measurement wave respectively onto the first and second regions in the measured sample X, and generates a difference measurement wave, which is the difference between the first reflected wave of the measurement wave that was reflected by the first region or the first transmitted wave of the measurement wave that was transmitted through the first region and the second reflected wave of the measurement wave that was reflected by the second region or the second transmitted wave of the measurement wave that was transmitted through the second region, by using the difference measurement wave as the first reflected wave or the first transmitted wave as is and as the second reflected wave or the second transmitted wave as is. Accordingly, with the semiconductor carrier lifetime measuring apparatus A2 of the second embodiment, the function as the measurement wave irradiation unit which irradiates a predetermined measurement wave respectively onto the first and second regions in the measured sample X, and the function as the difference measurement wave generation unit which generates a difference measurement wave, which is the difference between the first reflected wave of the measurement wave that was reflected by the first region or the first transmitted wave of the measurement wave that was transmitted through the first region and the second reflected wave of the measurement wave that was reflected by the second region or the second transmitted wave of the measurement wave that was transmitted through the second region, by using the difference measurement wave as the first reflected wave or the first transmitted wave as is and as the second reflected wave or the second transmitted wave as is, can be realized by being integrally configured as the measurement wave I/O unit 102.

This kind of measurement wave I/O unit 102 comprises, as shown in FIG. 9, for instance, a measurement wave generation unit 1020, a branching part 1021, first to fifth waveguides 1022 to 1026, and a branching/synthesizing unit 1027.

The measurement wave generation unit 1020 is a device which generates the predetermined measurement wave according to the control of the calculation control unit 104. With the semiconductor carrier lifetime measuring apparatus A2 of this embodiment, the predetermined measurement wave may be an electromagnetic wave since the conductivity change of the semiconductor that occurs during the course of generation/extinction of the excess carrier is extracted based on the intensity change of the measurement wave, in this embodiment it is a microwave, and the measurement wave generation unit 1020 is configured by comprising, for example, a microwave oscillator configured from a Gunn diode of 26 GHz or the like for generating a microwave. The measurement wave generation unit 1020 is connected to the branching part 1021.

The branching part 1021 is a device for branching (distributing) the entering measurement wave into two, and is configured, for example, by comprising a directional coupler such as a 10 dB coupler. This directional coupler is a waveguide having, for example, three first to third ports, and the microwave that entered the first port is output from the third and fourth ports, respectively, at a constant intensity ratio. The branching part 1021 is connected to the branching/synthesizing unit 1027 via the first waveguide 1022, and additionally connected to the detection unit 103 via the second waveguide 1023.

The first to fifth waveguides 1022 to 1026 are members which form the propagation path for guiding the measurement wave, and, in this embodiment, since the measurement wave is a microwave, the first to fifth waveguides 1022 to 1026 are a microwave waveguide.

The branching/synthesizing unit 1027 is a device which branches (distributes) the measurement wave (the one measurement wave) that entered from the branching part 1021 via the first waveguide 1022 into two in order to irradiate the measurement wave onto the first and second regions, respectively, in the measured sample X, and generates a difference measurement wave, which is the difference between the first reflected wave of the measurement wave that was reflected by the first region or the first transmitted wave of the measurement wave that was transmitted through the first region in the measured sample X and the second reflected wave of the measurement wave that was reflected by the second region or the second transmitted wave of the measurement wave that was transmitted through the second region in the measured sample X, by using the first reflected wave or the first transmitted wave as is and the second reflected wave or the second transmitted wave as is. In this embodiment, in order to configure the branching/synthesizing unit 1027 with fewer components, the branching/synthesizing unit 1027 of this embodiment is a device which branches (distributes) the measurement wave (the one measurement wave) that entered from the branching part 1021 via the first waveguide 1022 into two in order to irradiate the measurement wave onto the first and second regions, respectively, in the measured sample X, and generates a difference measurement wave, which is the difference between the first reflected wave of the measurement wave that was reflected by the first region in the measured sample X and the second reflected wave of the measurement wave that was reflected by the second region in the measured sample X, by using the first reflected wave as is and the second reflected wave as is. This kind of branching/synthesizing unit 1027 may be configured by combining a plurality of branching waveguides, but with the semiconductor carrier lifetime measuring apparatus A2 of this embodiment, for instance, a magic T-type waveguide 1027 is used. This magic T-type waveguide 1027 is structured, for example, as shown in FIG. 10, as an element with four openings; namely, four first to fourth ports 1027a to 1027d, and can be obtained by combining an E-surface T-branching waveguide and an H-surface T-branching waveguide. The microwave that entered the second port 1027b is distributed and output in a reverse phase and at equal power from the respective third and fourth ports 1027c, 1027d. Contrarily, with the respective microwaves that entered the third and fourth ports 1027c, 1027d, the difference between the respective microwaves is output from the second port 1027b, and the sum thereof is output from the first port 1027a. Accordingly, the magic T-type waveguide 1027 can generate a microwave of the difference between the respective microwaves in a microwave condition (as a microwave). The first waveguide 1022 is connected to the first port 1027a of the magic T-type waveguide 1027, the fifth waveguide 1026 is connected to the second port 1027b, the third waveguide 1024 is connected to the third port 1027c, and the fourth waveguide 1025 is connected to the fourth port 1027d.

The third waveguide 1024 is used for guiding the one measurement wave in order to irradiate (send) the one measurement wave that was branched by the branching/synthesizing unit 1027 onto the first region of the measured sample X, receiving the measurement wave that interacted with the measured sample X, which is the first reflected wave of the measurement wave that was reflected by the first region of the measured sample X in this embodiment, and once again guiding the received first reflected wave of the measurement wave or the first transmitted wave to the branching/synthesizing unit 1027. Thus, the tip of the third waveguide 1024 is provided with a first waveguide antenna 1024a. This first waveguide antenna 1024a is an antenna which irradiates the one measurement wave that arrived by propagating through the third waveguide 1024 onto the measured sample X, receives the measurement value that interacted with the measured sample X, and guides this to the third waveguide 1024. The first waveguide antenna 1024a is disposed along the normal direction of the measured sample X as shown in FIG. 11, the third waveguide 1024 is provided in an extending manner to the side face of one end, and comprises the opening 1024b at the other end. The opening 1024b is an opening for irradiating (sending) the one measurement wave onto the measured sample X, and receiving the measurement wave that interacted with the measured sample X. In addition, the one end of the first waveguide antenna 1024a comprises an opening 1024c for guiding the first light irradiated from the first light irradiation unit 101A into the first waveguide antenna 1024a in order to guide the one measurement wave, as well as the first light irradiated from the first light irradiation unit 1A, to the first region of the measured sample X. In this embodiment, since the measurement wave is a microwave, the first waveguide antenna 1024a is a microwave antenna.

Similarly, the fourth waveguide 1025 is used for guiding the other measurement wave in order to irradiate (send) the other measurement wave that was branched by the branching/synthesizing unit 1027 onto the second region of the measured sample X, receiving the measurement wave that interacted with the measured sample X, which is the second reflected wave of the measurement wave that was reflected by the second region of the measured sample X in this embodiment, and once again guiding the received second reflected wave of the measurement wave or the second transmitted wave to the branching/synthesizing unit 1027. Thus, the tip of the fourth waveguide 1025 is provided with a second waveguide antenna 1025*a*. This second waveguide antenna 1025*a* is an antenna which irradiates the other measurement wave that arrived by propagating through the fourth waveguide 1025 onto the measured sample X, receives the measurement value that interacted with the measured sample X, and guides this to the fourth waveguide 1025. The second waveguide antenna 1025*a*, as with the first waveguide antenna 1024*a*, is disposed along the normal direction of the measured sample X, the fourth waveguide 1025 is provided in an extending manner to the side face of one end, and comprises the opening 1025*b* at the other end. The opening 1025*b* is an opening for irradiating (sending) the other measurement wave onto the measured sample X, and receiving the measurement wave that interacted with the measured sample X. In addition, the one end of the second waveguide antenna 1025*a* comprises an opening 1025*c* for guiding the second light irradiated from the second light irradiation unit 101B into the second waveguide antenna 1025*a* in order to guide the other measurement wave, as well as the second light irradiated from the second light irradiation unit 101B, to the second region of the measured sample X. In this embodiment, since the measurement wave is a microwave, the second waveguide antenna 1025*a* is a microwave antenna.

The fifth waveguide 1026 is connected to the second port 1027*b* of the branching/synthesizing unit 1027, the magic T-type waveguide 1027 in this embodiment, and is used for guiding the difference measurement wave of the reflected microwave from the third waveguide 1024 and the fourth waveguide 1025 to the detection unit 103.

The detection unit 103 is a device for detecting the difference measurement wave that is generated by the measurement wave I/O unit 102 and is configured, for example, by comprising a mixer 1030 and a detector 1031. The detection results (the intensity of the difference measurement wave) of the difference measurement wave detected by the detection unit 103 are output to the calculation control unit 104.

The mixer 1030 is connected to the branching part 1021 via the second waveguide 1023 and connected to the branching/synthesizing unit 1027 via the fifth waveguide 1026, and is used for detecting the difference measurement wave based on the measurement wave by mixing (multiplying, multiplexing) the measurement wave from the measurement wave generation unit 1020 that was guided by the second waveguide 1023 and the difference measurement wave that was guided by the fifth waveguide 1026. The detector 1031 is connected to the mixer 1030, and is used for detecting the intensity of the detection signal that was detected by the mixer 1030. The intensity of the difference measurement wave is thereby detected. The detector 1031 outputs the detection results to the calculation control unit 104.

The calculation control unit 104 is a device which governs the overall control of the semiconductor carrier lifetime measuring apparatus A2 by controlling the respective components of the semiconductor carrier lifetime measuring apparatus A2 according to their functions and is configured, for example, by comprising a microcomputer including a microprocessor, a memory and the like. In addition, the calculation control unit 104 obtains the carrier lifetime in the measured sample X based on the detection results that were detected by the detection unit 103.

The move part 105 is a device for moving the measured sample X in the XY plane (horizontal plane) according to the control of the calculation control unit 104 so as to move the measurement location and is configured, for example, by comprising a stage 1050 and a stage control unit 1051. The stage 1050 is a mechanism for mounting the measured sample X and moving the measured sample X on the XY plane, and the stage control unit 1051 is used for driving and controlling the stage 1050 so that the predetermined position in the measured sample X can be measured according to the control of the calculation control unit 104.

Note that the configuration may also be such that a third waveguide antenna for receiving the first transmitted wave of the measurement wave that was transmitted through the first region is provided to the opening 1024*b* of the first waveguide antenna 1024*a* at an opposing position via the measured sample X, a fourth waveguide antenna for receiving the second transmitted wave of the measurement wave that was transmitted through the second region is provided to the opening 1025*b* of the second waveguide antenna 1025*a* at an opposing position via the measured sample X, a synthesizing unit which generates the difference measurement wave, which is the difference between the first transmitted wave of the measurement wave that was received by the third waveguide antenna and the second transmitted wave of the measurement wave that was received by the fourth waveguide antenna, by using the first transmitted wave as is and the second transmitted wave as is, is provided, and the difference measurement wave that was synthesized by the synthesizing unit is guided to the mixer 1030 of the detection unit 103.

The semiconductor carrier lifetime measuring apparatus A2 configured as described above measures the carrier life of the semiconductor, for example, based on the following operations. Foremost, contamination and surface damage on the surface of the semiconductor wafer to be measured are foremost removed in advance via, for instance, so-called chemical etching (washing treatment), whereby achieved is a state where a natural oxide film has been applied. In addition, the semiconductor wafer that was subject to the foregoing washing treatment is thereafter placed, as the measured sample X, on the stage 1050.

In addition, for example, when a start switch not shown for inputting a command for starting the measurement into the semiconductor carrier lifetime measuring apparatus A2 is operated, the measurement of the carrier lifetime of the measured sample X by the semiconductor carrier lifetime measuring apparatus A2 is started, and, in order to measure a predetermined measurement location, the stage 1050 is driven and controlled by the stage control unit 1051 according to the control of the calculation control unit 104, and the measured sample X is moved to a predetermined position.

Subsequently, when the measured sample X is moved to a predetermined position by the move part 105, the measurement wave is irradiated onto the respective first and second regions by the measurement wave I/O unit 102 according to the control of the calculation control unit 104, the first and second light are irradiated onto the first and second regions of the measured sample X by the respective first and second light irradiation units 101A, 101B according to the control of the calculation control unit 104, the difference measurement wave, which is the difference between the measurement wave that interacted with the measured sample X in the first region and the measurement wave that interacted with the measured sample X in the second region, is directly generated, the difference measurement wave is detected by the detection unit 103, and the detection results are output from the detection unit 103 to the calculation control unit 104.

More specifically, in the measurement wave I/O unit 102, the measurement wave is generated by the measurement wave generation unit 1020 according to the control of the calculation control unit 104, and the generated measurement wave is output from the measurement wave generation unit 1020 to the branching part 1021. The measurement wave is branched into two by the branching part 1021, and one measurement wave (1st-1st measurement wave) is output to the branching/synthesizing unit 1027 via the first waveguide 1022, and the other measurement wave (1st-2nd measurement wave) is output to the mixer 1030 of the detection unit 103 via the second waveguide 1023. The measurement wave (1st-1st measurement wave) that entered the branching/synthesizing unit 1027 (first port 1027*a* of the magic T-type waveguide 1027) from the branching part 1021 via the first waveguide 1022 is branched in-phase and at equal power, and the one branched measurement wave (1st-1st measurement wave) is output from the branching/synthesizing unit 1027 (third port 1027*c* of the magic T-type waveguide 1027) to the third waveguide 1024, and the other branched measurement wave (2nd-2nd measurement wave) is output from the branching/synthesizing unit 1027 (fourth port 1027*d* of the magic T-type waveguide 1027) is output to the fourth waveguide 1025. The one measurement wave (2nd-1st measurement wave) that was branched by the branching/synthesizing unit 1027 is guided by the third waveguide 1024 and irradiated onto the first region of the measured sample X from the first waveguide antenna 1024*a*, and the other measurement wave (2nd-2nd measurement wave) that was branched by the branching/synthesizing unit 1027 is guided by the fourth waveguide 1025 and irradiated onto the second region of the measured sample X from the second waveguide antenna 1025*a*.

The measurement wave that interacted with the measured sample X at the first region, the first reflected wave of the measurement wave that was reflected by the first region in the configuration shown in FIG. 9, is received by the first waveguide antenna 1024*a*, guided by the third waveguide 1024, and once again enters the branching/synthesizing unit 1027 (third port 1027*c* of the magic T-type waveguide 1027). The measurement wave that interacted with the measured sample X at the second region, the second reflected wave of the measurement wave that was reflected by the second region in the configuration shown in FIG. 9, is received by the second waveguide antenna 1025*a*, guided by the fourth waveguide 1025, and once again enters the branching/synthesizing unit 1027 (fourth port 1027*d* of the magic T-type waveguide 1027). In addition, the first reflected wave and the second reflected wave are synthesized by the branching/synthesizing unit 1027 (magic T-type waveguide 1027) in a microwave state, and the difference measurement wave as the difference between the first reflected wave and the second reflected wave is output from the branching/synthesizing unit 1027 (second port 1027*b* of the magic T-type waveguide 1027) to the mixer 1030 of the detection unit 103 via the fifth waveguide 1026.

In addition, in the detection unit 103, the measurement wave (1st-2nd measurement wave) from the measurement wave generation unit 1020 that was guided by the second waveguide 1023 and the difference measurement wave that was guided by the fifth waveguide 1026 are mixed (multiplied, multiplexed) by the mixer 1030, and the difference measurement wave is detected as the measurement wave. The detection signal that was detected by the mixer 1030 is output to the detector 1031, and its intensity (level) is thereby detected. The intensity (level) of the difference measurement wave is thereby detected. The intensity of the difference measurement wave (detection results) detected by the detector 1031 are output to the calculation control unit 104.

Meanwhile, with respect to the light irradiation unit 1, the first light is generated by the first light source unit 1010A according to the control of the calculation control unit 104 in the first light irradiation unit 101A, and the generated first light is output from the first light source unit 1010A to the first light intensity regulator 1011A. The light intensity (level) of the first light is adjusted to a predetermined light intensity by the first light intensity regulator 1011A so that the initial first excess carrier mass based on the irradiation of the first light becomes equal to the initial second excess carrier mass based on the irradiation of the second light, and the adjusted first light is output from the first light intensity regulator 1011A to the first mirror 1012A. The light path of this first light is bent substantially 90 degrees by the first mirror 1012A and reflected toward the measured sample X, and the reflected first light is output from the first mirror 1012A to the first lens 1013A. This first light is subject to the lens effect of the first lens 1013A, and the first light that was subject to this lens effect is irradiated onto the first region of the measured sample X through the first waveguide antenna 1024*a* of the third waveguide 1024. Based on the lens effect of the first lens 1013A, the first region of the measured sample X is irradiated by the first light substantially evenly and with substantially broad irradiation. Thus, the semiconductor carrier lifetime measuring apparatus A2 can reduce the diffusion of the excess carriers in the in-plane direction.

Similarly, the second light is generated by the second light source unit 1010B according to the control of the calculation control unit 104 in the second light irradiation unit 101B, and the generated second light is output from the second light source unit 1010B to the second light intensity regulator 1011B. The light intensity (level) of the second light is adjusted to a predetermined light intensity by the second light intensity regulator 1011B so that the initial second excess carrier mass based on the irradiation of the second light becomes equal to the initial first excess carrier mass based on the irradiation of the first light, and the adjusted second light is output from the second light intensity regulator 1011B to the second mirror 1012B. The light path of this second light is bent substantially 90 degrees by second mirror 1012B and reflected toward the measured sample X, and the reflected second light is output from the second mirror 1012B to the second lens 1013B. This second light is subject to the lens effect of the second lens 1013B, and the second light that was subject to this lens effect is irradiated onto the second region of the measured sample X second waveguide antenna 25*a* of the fourth waveguide 25. Based on the lens effect of the second lens 1013B, the second region of the measured sample X is irradiated by the first light substantially evenly and with substantially broad irradiation. Thus, the semiconductor carrier lifetime measuring apparatus A2 can reduce the diffusion of the excess carriers in the in-plane direction.

Note that the first light intensity regulator 1011A and the second light intensity regulator 1011B are adjusted in advance prior to the measurement by actually irradiating the first light and the second light onto the measured sample X so that the initial first and second excess carrier mass are generated at the same level, which are generated when two types of light having mutually different wavelengths are irradiated onto the first and second regions in the measured sample X, respectively.

Accordingly, if the measurement wave is irradiated onto the measured sample X while the first and second light are respectively irradiated onto the first and second regions of the measured sample X, the first reflected wave of the measurement wave in the first region based on the first light is received by the first waveguide antenna 1024*a* of the third waveguide 1024, and guided to the branching/synthesizing unit 1027 (magic T-type waveguide 1027) via the third waveguide 1024.

In addition, the second reflected wave of the measurement wave in the second region based on the second light is received by the second waveguide antenna 1025a of the fourth waveguide 1025, and guided to the branching/synthesizing unit 1027 (magic T-type waveguide 1027) via the fourth waveguide 1025. In addition, the first reflected wave and the second reflected wave of the measurement wave in cases where the branching/synthesizing unit 1027 (magic T-type waveguide 1027) irradiates the first and second light onto the first and second regions of the measured sample X are synthesized, in a microwave state, with the difference measurement wave as the difference between the first reflected wave and the second reflected wave of the measurement wave. This difference measurement wave is output to the detection unit 103 via the fifth waveguide 1026, detected by the detection unit 103, and the detected intensity of the difference measurement wave is incorporated into the calculation control unit 104. Normally, the intensity of the difference measurement wave change is measured immediately after the irradiation/extinction (immediately after irradiating and turning off) the first and second light of the pulsed laser beam by irradiating the measurement wave onto the measured sample X, and irradiating the first and second light of the pulsed laser beam, respectively, while irradiating the measurement wave onto the first and second regions of the measured sample X, respectively.

Subsequently, the calculation control unit 104 calculates and obtains the carrier lifetime of the object to be measured using a well-known common means based on the difference measurement wave. The carrier lifetime at the predetermined location in the measured sample X is thereby measured, and, with the semiconductor carrier lifetime measuring apparatus A2, the stage 1050 is driven and controlled by the stage control unit 1051 according to the control of the calculation control unit 104 so as to measure the carrier lifetime at the next predetermined location in the measured sample X, the measured sample X is thereby moved to the next predetermined position, and the foregoing operation is repeated. Accordingly, the semiconductor carrier lifetime measuring apparatus A2 scans the entire surface of the measured sample X at predetermined intervals to obtain the carrier lifetime, and measures the carrier lifetime across the entire surface of the measured sample X. This carrier lifetime is a measurement value of the region including the first and second regions.

In addition, the semiconductor carrier lifetime measuring apparatus A2 outputs the obtained bulk carrier lifetime to, for example, an output device not shown such as a display device or a printing device.

Figure 12:
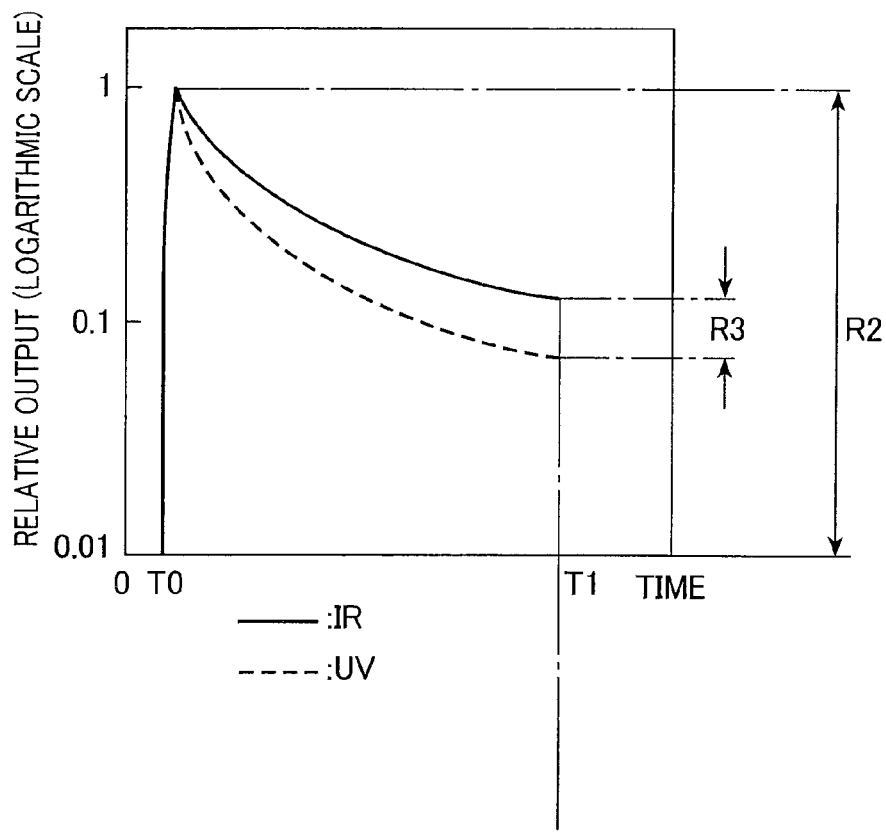
FIG. 12 is a diagram showing the change in the temporal relative output in the reflected wave of the measurement wave.
Figure 13:
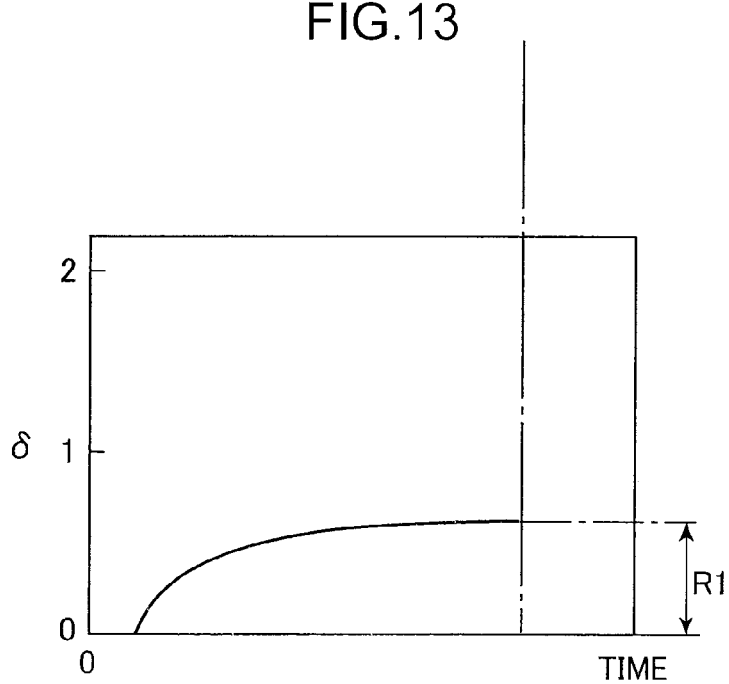
FIG. 13 is a diagram showing the time change of the relative output difference (difference measurement wave) of the reflected wave of the measurement wave that is obtained upon respectively irradiating infrared light and ultraviolet light to the semiconductor.

FIG. 12 is a diagram showing the changes of the temporal relative output in the reflected wave of the measurement wave. The horizontal axis of FIG. 12 shows the elapsed time, and its vertical axis shows the intensity (level) of the relative output based on a logarithmic scale. In FIG. 12, the solid line shows the time change of the relative output in cases where infrared light is irradiated onto the semiconductor, and the broken line shows the time change of the relative output in cases where ultraviolet light is irradiated onto the semiconductor. FIG. 13 is a diagram showing the time change of the relative output difference (difference measurement wave) of the reflected wave of the measurement wave in cases where infrared light and ultraviolet light are respectively irradiated onto the semiconductor. The horizontal axis of the FIG. 13 shows the elapsed time, and its vertical axis shows the intensity (level) of the relative output difference (difference measurement wave).

Generally speaking, the intensity (relative output) of the reflected wave of the measurement wave becomes maximum substantially immediately after the irradiation/extinction of light as shown in FIG. 12, and, thereafter, decreases with the lapse of time, and eventually becomes substantially constant when the carrier enters a state of thermal equilibrium. In addition, during the course that the reflected wave intensity decreases, the decrease ratio (rate of decrease, amount of decrease per unit time) is relatively large initially, and decreases with the lapse of time. Moreover, the temporal intensity change of the reflected wave caused by the infrared laser beam (IR, solid line in FIG. 12) of the first light is smaller than the temporal intensity change of the reflected wave caused by the ultraviolet laser beam (UV, broken line in FIG. 12) of the second light. In addition, as shown in FIG. 13, the difference (intensity of the difference measurement wave) $\delta$ between the intensity of the reflected wave caused by the infrared laser beam (IR) of the first light and the intensity of the reflected wave caused by the ultraviolet laser beam (UV) of the second light decreases with the lapse of time, and eventually becomes substantially constant. Note that FIG. 12 and FIG. 13 are standardized with the maximum value substantially immediately after the irradiation/extinction of light.

This difference (intensity of the difference measurement wave) $\delta$ is dependent on the surface recombination velocity S, and the greater this difference (intensity of the difference measurement wave) $\delta$, the greater the surface recombination velocity S, and the surface recombination velocity S can be obtained from this difference (intensity of the difference measurement wave) $\delta$. More specifically, normally, the relationship ($\delta$-S/D table) with S/D obtained by dividing this difference (intensity of the difference measurement wave) $\delta$ and the surface recombination velocity S by the diffusion velocity D is obtained in advance, a value in which the $\delta$ value becomes substantially constant is obtained as described above, S/D is obtained as a result of the S/D corresponding to the $\delta$ value which became constant being referred to from the $\delta$-S/D table, the surface recombination velocity S is obtained by multiplying the pre-obtained diffusion coefficient D by, for example, $D=30$ cm$^2$/s, and the carrier lifetime is thereby obtained.

Conventionally, a detector detected the first reflected wave of the measurement wave, subsequently detected the second reflected wave of the measurement wave, and obtained the $\delta$ value based on the difference in the foregoing detection results. Thus, the respective first and second reflected waves of the measurement wave are measured with the overall dynamic range of the detector. Specifically, a range from the level of 0 to the level of maximum value in the first reflected value of the measurement wave is measured with the overall dynamic range of the detector. Consequently, as shown in FIG. 12, when the first and second reflected waves of the measurement wave are respectively measured across a range R2 in the overall dynamic range of the detector, the difference in the respective detection results will be a range R3 which is smaller (narrower) than the range R2 (R3<R2), and it was not possible to effectively use the overall dynamic range of the detector. For example, if the range R2 is 10 bits (=1024), the range R3 was several bits thereamong; for instance, 3 bits (=8). The range R3 will be smaller as the difference between the intensity of the first reflected wave and the intensity of the second reflected wave is smaller, and the overall dynamic range of the detector cannot be effectively used.

Meanwhile, with the semiconductor carrier lifetime measuring apparatus A2 of this embodiment, the difference measurement wave as the difference between the first reflected wave and the second reflected wave is generated directly as a microwave, and the difference measurement wave of the microwave is detected by the detector. Specifically, a range from the level of 0 to the level of maximum value in the difference measurement wave is measured with the overall dynamic range of the detector. Accordingly, as shown in FIG. 13, this difference measurement wave can be detected by using the overall dynamic range of the detector, and a range R1 that is equivalent to the range R2 can be detected in the overall dynamic range of the detector. In other words, in comparison to the foregoing example, the difference measurement wave will be detected at 10 bits (=1024), which is equivalent to the range R2.

Accordingly, with the semiconductor carrier lifetime measuring apparatus A2 of this embodiment, a difference measurement wave, which is the difference between the first reflected wave of the measurement wave that was reflected by the first region or the first transmitted wave of the measurement wave that was transmitted through the first region in the measured sample X and the second reflected wave of the measurement wave that was reflected by the second region or the second transmitted wave of the measurement wave that was transmitted through the second region in the measured sample X, is generated as a result of the branching/synthesizing unit 1027 using the first reflected wave or the first transmitted wave as is and using the second reflected wave or the second transmitted wave as is, the difference measurement wave is detected by the detection unit 103, and the carrier lifetime is obtained based on the detection results. Thus, since the number of significant figures of the detection results corresponding to the difference between the respective measurement results obtained by directly measuring the difference measurement wave with the detector will directly detect the difference measurement wave using the entire dynamic range in the detector than the number of significant figures in the difference between the respective measurement results that were calculated by obtaining the difference of the first measurement result obtained by measuring the first reflected wave or the first transmitted wave with a predetermined detector and the second measurement result obtained by measuring the second reflected wave or the second transmitted wave with the detector, there will be a greater number of significant figures. Accordingly, the semiconductor carrier lifetime measuring apparatus A2 of this embodiment can more accurately measure the carrier lifetime.

Generally speaking, when light is irradiated onto a semiconductor, the light (incident light) will penetrate the semiconductor, but the length of penetration will depend on the wavelength of the incident light. With the semiconductor carrier lifetime measuring apparatus A2 of this embodiment, the first and second light are two lights selected among infrared light having a wavelength of an infrared region, visible light having a wavelength of a visible region, and ultraviolet light having a wavelength of an ultraviolet region. Thus, since the wavelength difference of these lights is great, the difference in their lengths of penetration will also increase. It is thereby possible to cause the ratio of influence caused by the surface recombination contained in the first and second reflected waves based on the respective lights, to differ considerably. Otherwise, it is also possible to cause the ratio of influence caused by the surface recombination contained in the first and second transmitted waves of the measurement wave to differ considerably. Accordingly, the semiconductor carrier lifetime measuring apparatus A2 of this embodiment can more accurately measure the carrier lifetime in comparison to conventional technology.

Moreover, with the semiconductor carrier lifetime measuring apparatus A2 of this embodiment, the respective light intensities of the first and second light are adjusted by the first and second light intensity regulators 1011A, 1011B, respectively, so that the initial first and second excess carrier mass that are generated when the first and second light are irradiated onto the first and second regions, respectively, become mutually equal. Thus, since the initial first and second excess carrier masses become mutually substantially equal, for instance, the output signal level of the detector 1031 can be made to be zero in cases where the surface recombination velocity S is zero, and the carrier lifetime can be measured even more accurately. Moreover, in the foregoing case, with R<<$\Delta$1, $\Delta$2, the intensity R1 of the first reflected wave is represented as R1=R+$\Delta$1, the intensity R2 of the second reflected wave is represented as R2=R+$\Delta$2, and, initially, since R1 and R2 will substantially coincide (R1~R2), $\delta$=ln (R1/R2)=ln ((R+$\Delta$1)/(R+$\Delta$2))~ln(R−$\Delta$), $\Delta$=$\Delta$1−$\Delta$2 is obtained, and the $\delta$ can be directly calculated based on the detection results of the difference measurement wave. Note that the symbol "~" used in this paragraph shows that the two are mathematically approximate.

Another embodiment is now explained.

(Third Embodiment)

With the semiconductor carrier lifetime measuring apparatus A2 of the second embodiment, as described above, the surface recombination velocity S was obtained by using a known value of the diffusion coefficient D as the obtained S/D; for instance, D=30 cm$^2$/s, and the carrier lifetime was subsequently obtained. Nevertheless, there are cases where the diffusion coefficient D is not necessarily known. In particular, when the carrier concentrations of electrodes and holes are n and p, respectively, and the diffusion coefficients D of electrodes and holes are Dn and Dp, respectively, the actual diffusion coefficient D is given as (n+p)/(n/Dp+p/Dn), and this is dependent on the carrier concentration or conduction. Thus, the semiconductor carrier lifetime measuring apparatus A3 of the third embodiment is configured by combining the semiconductor carrier lifetime measuring apparatus A2 of the second embodiment and the semiconductor carrier lifetime measuring apparatus A1 of first embodiment, and obtains the carrier lifetime even more accurately by also measuring the diffusion coefficient D.

Figure 14A:
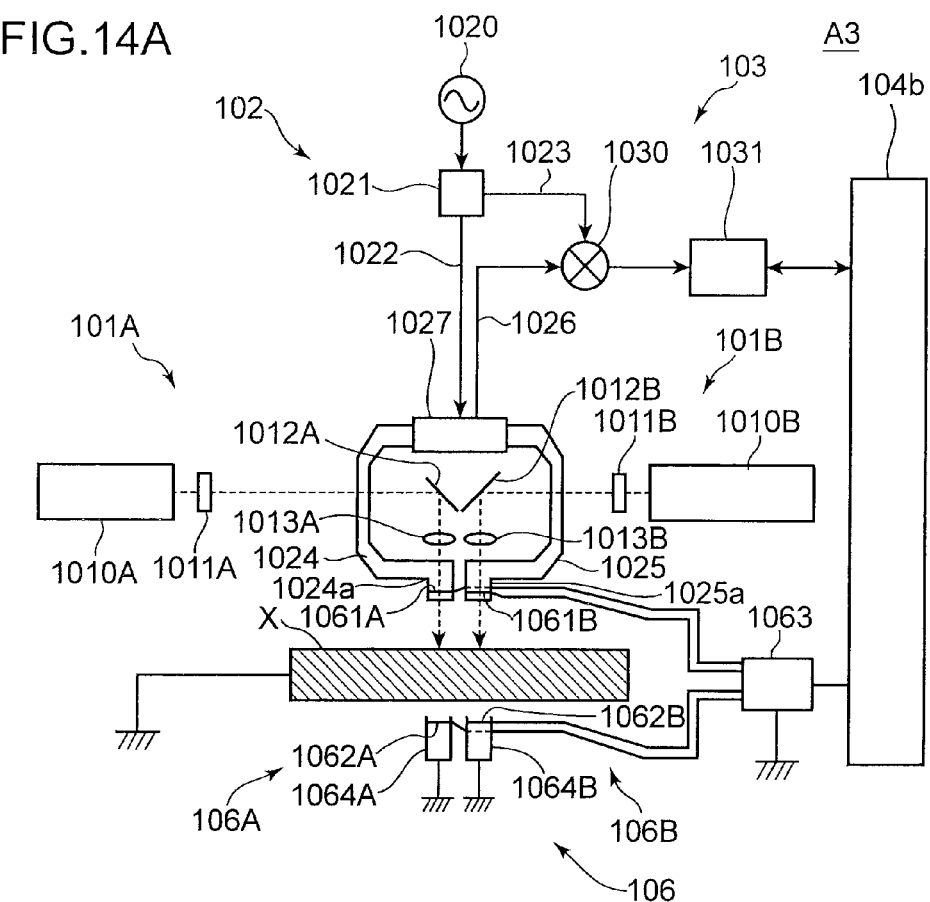
FIGS. 14A and 14B are diagrams showing the configuration of the semiconductor carrier lifetime measuring apparatus in the third embodiment.
Figure 14B:
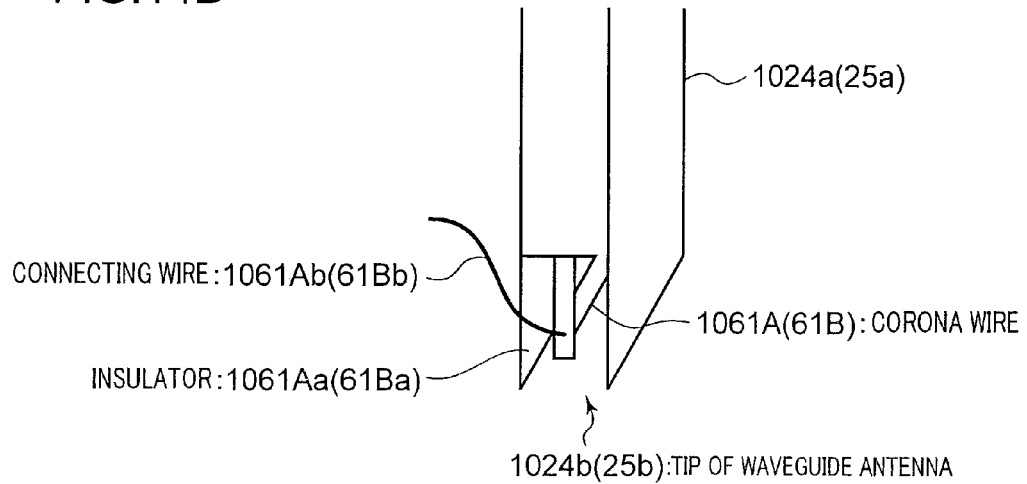

The carrier lifetime measuring apparatus A3 according to the third embodiment is now explained in further detail. FIG. 14 are diagrams showing the configuration of the semiconductor carrier lifetime measuring apparatus of the third embodiment. FIG. 14A is a diagram showing the overall configuration, and FIG. 14B is a partial enlarged perspective view showing the tip part of the waveguide antenna.

The semiconductor carrier lifetime measuring apparatus A3 in the third embodiment is configured by comprising, for example, as shown in FIG. 14A, a light irradiation unit 101 (101A, 101B), a measurement wave I/O unit 2, a detection unit 103, a calculation control unit 104b, and a discharge unit 106, and further comprises a move part 105 not shown in FIG. 14 for moving the measurement location. Since the light irradiation unit 101 (101A, 101B), the measurement wave I/O unit 102, the detection unit 103 and the move part 105 in the semiconductor carrier lifetime measuring apparatus A3 of the third embodiment are configured the same as the light irradiation unit 101 (101A, 101B), the measurement wave I/O unit 102, the detection unit 103 and the move part 105 in the semiconductor carrier lifetime measuring apparatus A2 of the second embodiment, the explanation thereof is omitted. Note that, with the move part 105 in the carrier lifetime measuring apparatus A3 of the third embodiment, since a corona wire 1062 is also disposed at the rear face in addition to the surface of the measured sample X as described later, the stage 105 is of a structure which supports the measured sample X at the edge of the measured sample X, and, for example, is configured by comprising a hollow cylindrical body in the shape of circle or rectangle in a horizontal sectional view.

The discharge unit 106 is a device for causing the surface recombination velocity of the measured sample X to change from the first surface recombination velocity condition to the second surface recombination velocity condition, which is different from the first surface recombination velocity condition, according to the control of the calculation control unit 104*b*, a device for causing the surface of the measured sample X to become at least two or more different surface recombination velocity conditions, and corresponds to an example of the surface recombination velocity changing unit. In this embodiment, the discharge unit 106 is, for example, a corona discharge generating device which generates a corona discharge and applies this corona discharge to the first and second regions of the measured sample X onto which the measurement wave is irradiated by the measurement wave I/O unit 2, and corresponds to an example of the corona discharge application unit. In this embodiment, the discharge unit 106 comprises a first corona discharge unit 106A as with the first embodiment which applies a corona discharge to the first region of the measured sample X and a second corona discharge unit 106B as with the first embodiment which applies a corona discharge to the second region of the measured sample X in order to apply a corona discharge to the two regions of the first and second regions. More specifically, the first corona discharge unit 106A is configured, for example, as shown in FIGS. 14A and 14B, by comprising an eleventh corona wire 1061A as a first electrode which is subject to a corona discharge when a high voltage is applied to the vicinity of the opening 1024*b* of the third waveguide antenna 1024*a*, a twelfth corona wire 1062A—a second electrode—which is subject to a corona discharge when a high voltage is applied to the vicinity of the rear face (rear face region) of the measured sample X facing the first region of the measured sample X onto which the measurement wave is irradiated, a power source unit 1063 which generates the high voltage for supplying the high voltage to eleventh and twelfth corona wires 1061A, 1062A, respectively, and a mounting member 1064A for mounting the twelfth corona wire 1062A near the rear face region. Similarly, as shown in FIG. 14A, the second corona discharge unit 106B is configured by comprising a twenty-first corona wire 1061B as a first electrode which is subject to a corona discharge when a high voltage is applied to the vicinity of the opening 1025*a* of the fourth waveguide antenna 1025*a*, a twenty-second corona wire 1062B—a second electrode—which is subject to a corona discharge when a high voltage is applied to the vicinity of the rear face (rear face region) of the measured sample X facing the second region of the measured sample X onto which the measurement wave is irradiated, a power source unit 1063 which generates the high voltage for supplying the high voltage to twenty-first and twenty-second corona wires 1061B, 1062B, respectively, and a mounting member 1064B for mounting the twenty-second corona wire 1062B near the rear face region.

These eleventh, twelfth, twenty-first and twenty-second corona wires 1061A, 1062A; 1061B, 1062B are, for example, tungsten wire or the like having a wire diameter of 0.1 mm. In FIG. 14B, the waveguide antenna 1024*a* is, for example, an angular tube, a part of the two surfaces of the opening 1024*b* facing each other is cut out, and a predetermined insulator 1061Aa is provided to each of the cutout portions. In addition, the eleventh corona wire 1061A is mounted so as to cut across the center of the opening 1024*b* by causing it to cross over the two facing insulators 1061Aa (FIG. 14B shows only one insulator 1061Aa). Moreover, the eleventh corona wire 1061 is connected to the power source unit 1063 via the connecting wire 1061Ab, and the eleventh corona wire 1061 and the waveguide antenna 1024*a* are insulated thereby. The twelfth corona wire 1062A is similarly insulated and mounted by the mounting member 1064. Moreover, the same applies to the twenty-first corona wire 1061B and the twenty-second corona wire 1062B. Moreover, in order to dispose the measured sample X between the eleventh corona wire 1061A and the twelfth corona wire 1062A and between the twenty-first corona wire 1061B and the twenty-second corona wire 1062B, the stage 105 not shown for supporting the measured sample X is provided. Based on the foregoing configuration, it is possible to apply a corona discharge, which was generated by using the power source unit 1063 to apply a predetermined voltage to the electrodes of the eleventh and twelfth corona wires 1061A, 1062A provided in the vicinity of the measured sample X and to the electrodes of the twenty-first and twenty-second corona wires 1061B, 1062B provided in the vicinity of the measured sample X, to the measured sample X.

The calculation control unit 104*b*, as with the calculation control unit 104, is a device which governs the overall control of the semiconductor carrier lifetime measuring apparatus A3 and is configured, for example, by comprising a microcomputer including a microprocessor, a memory and the like. In addition, the calculation control unit 104*b* comprises, as shown in FIG. 7, a calculation unit not shown which calculates the carrier lifetime based on the intensity of the difference measurement wave, which is the difference of the respective measurement waves that interacted with the measured sample X, that was detected by the measurement wave detection unit 103 as with the calculation unit 41 in the calculation control unit 4 of the semiconductor carrier lifetime measuring apparatus A1 of the first embodiment. The calculation unit functionally comprises a first condition calculation unit, a second condition calculation unit, a lifetime calculation unit, a diffusion coefficient storage unit, and a δ-S/D table storage unit, as with the calculation unit 41, as a result of, for example, executing the carrier lifetime calculation program for calculating the carrier lifetime based on the intensity of the reflected wave of the measurement wave (reflected measurement wave) that was detected by the measurement wave detection unit 103. Since these are the same as the first condition calculation unit 411, the second condition calculation unit 412, the lifetime calculation unit 413, the diffusion coefficient storage unit 414 and the δ-S/D table storage unit 415 in the calculation unit 41 of the first embodiment, the explanation thereof is omitted.

The semiconductor carrier lifetime measuring apparatus A3 configured as described above can measure the bulk carrier lifetime τb of the semiconductor by performing the following operations.

As with the semiconductor carrier lifetime measuring apparatus A1 of the first embodiment explained with reference to FIG. 4, foremost, the semiconductor wafer to be measured is subject to the washing treatment in advance, whereby achieved is a state where a natural oxide film has been applied. This state in which the natural oxide film has been applied is the first surface recombination velocity condition. In addition, the semiconductor wafer that was subject to the foregoing washing treatment is thereafter placed, as the measured sample X, on the stage 1050 (not shown in FIG. 14) of the move part 105, and is set at a predetermined measurement position that is sandwiched between the eleventh corona wire 1061A and the twelfth corona wire 1062A and sandwiched between the twenty-first corona wire 1061B and the twenty-second corona wire 1062B.

In addition, for example, when the start switch not shown is operated, the measurement of the carrier lifetime of the measured sample X by the semiconductor carrier lifetime measuring apparatus A3 is started, and, in order to measure a predetermined measurement location, the stage 1050 is driven and controlled by the stage control unit 1051 according to the control of the calculation control unit 104*b*, and the measured sample X is moved to a predetermined position.

Subsequently, S/D in the case where the measured sample X is in the first surface recombination velocity condition is obtained, and the diffusion coefficient D is obtained based on the obtained S/D. FIG. 15 is a flowchart showing the operation of the semiconductor carrier lifetime measuring apparatus of the third embodiment in cases of obtaining the diffusion coefficient.

More specifically, when the measured sample X is moved to a predetermined position by the move part 105, as shown in FIG. 15, the measurement wave is irradiated onto the respective first and second regions by the measurement wave I/O unit 102 according to the control of the calculation control unit 104*b* (S121), the first and second light are irradiated onto the first and second regions of the measured sample X by the respective first and second light irradiation units 101A, 101B according to the control of the calculation control unit 104*b*, the difference measurement wave, which is the difference between the measurement wave that interacted with the measured sample X in the first region and the measurement wave that interacted with the measured sample X in the second region, is directly generated, the difference measurement wave is detected by the detection unit 103 (S122), and the detection results are output from the detection unit 103 to the calculation control unit 104*b*.

In addition, the first condition calculation unit 10411 of the calculation unit 1041 obtains the δ value based on the output of the detection unit 103, obtains a value in which the δ value became substantially constant as described above, and, by referring to the δ-S/D table of the δ-S/D table storage unit 10415, obtains S/D corresponding to the value in which the δ value became substantially constant (S123). Subsequently, the first condition calculation unit 10411 of the calculation unit 1041 obtains α1 in the first surface recombination condition by using the obtained S/D in Formula 2 (S124). Subsequently, the first condition calculation unit 10411 of the calculation unit 1041 obtains the diffusion coefficient D by evaluating the bulk carrier lifetime τb relative to the diffusion coefficient D in the measured sample X by using Formula 5, which is a modification of Formula 1, and stores the obtained diffusion coefficient D in the diffusion coefficient storage unit 10414 (S125). In this processing, α in Formula 5 is α1.

Here, when the bulk carrier lifetime τb is a relatively large value such as 100 μs, preferably 1000 μs (=1 ms), the diffusion coefficient D becomes a value that coincides with the peak value of Formula 5.

For example, when S/D=4000 and the measurement result τ1=4 μs, the bulk carrier lifetime τb based on Formula 5 becomes the graph shown in FIG. 8 when the diffusion coefficient D is calculated across a predetermined range including the peak; for instance, across a range of 0 to 30, and the bulk carrier lifetime τb based on Formula 5 will have a peak at one point. The value at this peak (approximately 15.6 in the example of FIG. 8) will be the diffusion coefficient D.

Based on the respective processes described above, S/D in cases where the measured sample X is in the first surface recombination velocity condition is obtained, and the diffusion coefficient D is obtained based on the obtained S/D.

Subsequently, surface treatment of the measured sample X is performed based on the obtained diffusion coefficient D (approximately 15.6 in the example of FIG. 8). Preferably, this surface treatment is, for instance, corona discharge treatment, oxidation treatment, passivation treatment that is performed by depositing silicon nitride, amorphous silicon and alumina film, and so on. In this embodiment, since surface treatment can be temporarily performed only for the time that is required for the measurement and then returned to its original state after the measurement, corona discharge treatment is adopted as the surface treatment of the measured sample X. More specifically, the power source unit 1063 applies a high voltage of mutually different polarities to the eleventh and twelfth corona wires 1061A, 1062A according to the control of the calculation control unit 104*b*, and additionally applies a high voltage of mutually different polarities to the twenty-first and twenty-second corona wires 1061B, 1062B. Consequently, a corona discharge is provided from the eleventh and twelfth corona wires 1061A, 1062A, respectively, to both main surfaces of the measured sample X in the first region, whereby surface treatment is performed, and a corona discharge is provided from the twenty-first and twenty-second corona wires 1061B, 1062B, respectively, to both main surfaces of the measured sample X in the second region, whereby surface treatment is performed.

Subsequently, S/D in cases where the measured sample X is in the second surface recombination velocity condition is obtained, and the surface recombination velocity S is obtained based on the obtained S/D.

More specifically, as a result of performing the same processes as the respective processes of processing S21 and processing S22, which were explained with reference to FIG. 9, while applying a high voltage to the eleventh and twelfth and the twenty-first and twenty-second corona wires 1061A, 1062A; 1061B, 1062B by using the power source unit 1063, the difference measurement wave based on the first and second light is detected by the detection unit 103, and incorporated into the calculation unit 1041 of the calculation control unit 104*b*.

Subsequently, based on processing that is the same as processing S123 explained with reference to FIG. 15, the second condition calculation unit 10412 of the calculation unit 1041 obtains the δ value based on the output of the detection unit 103, obtains a value in which the δ value becomes substantially constant, and, by referring to the δ-S/D table of the δ-S/D table storage unit 10415, obtains S/D corresponding to the value in which the δ value becomes substantially constant.

Subsequently, the second condition calculation unit 10412 of the calculation unit 1041 obtains the surface recombination velocity S by multiplying the obtained S/D by the diffusion coefficient D obtained as described above.

Based on the respective processes described above, S/D in cases where the measured sample X is in the second surface recombination velocity condition is obtained, and the surface recombination velocity S is obtained based on the obtained S/D.

Subsequently, the lifetime calculation unit 10413 of the calculation unit 1041 obtains the bulk carrier lifetime τb by using Formula 1 and Formula 2 based on the obtained surface recombination velocity S.

In addition, the semiconductor carrier lifetime measuring apparatus A3 outputs the obtained bulk carrier lifetime τb to, for example, an output device not shown such as a display device or a printing device.

Note that, for the second measurement onward, by using the diffusion coefficient D that is stored in the diffusion coefficient storage unit 10414, the processing for obtaining the diffusion coefficient D in the foregoing first surface recombination velocity condition can be omitted, and the measurement can be started from the surface treatment for achieving the second surface recombination velocity condition.

As described above, the semiconductor carrier lifetime measuring apparatus A3 of this embodiment executes each of the following steps; namely, a first difference measuring step of measuring, by irradiating at least two types of light having mutually different wavelengths—irradiating the first and second light according to the present embodiment—while irradiating a predetermined measurement wave onto a semiconductor X to be measured when the semiconductor X to be measured is in a first surface recombination velocity condition, a first difference measurement wave, which is a difference between a first reflected wave or a first transmitted wave of the measurement wave in the first region in the semiconductor X to be measured and a second reflected wave or a second transmitted wave of the measurement wave in the second region in the semiconductor X to be measured; a first S/D calculation step of obtaining S/D in the first surface recombination velocity condition based on the first difference that was measured in the first difference measuring step when a surface recombination velocity in the semiconductor X to be measured is S and a diffusion coefficient is D; a diffusion coefficient calculation step of obtaining the diffusion coefficient D based on the S/D in the first surface recombination velocity condition that was obtained in the first S/D calculation step; a surface recombination velocity condition changing step of causing the semiconductor to be measured to change from the first surface recombination velocity condition to a second surface recombination velocity condition that is different from the first surface recombination velocity condition; a second difference measuring step of measuring, by irradiating the at least two types of light having mutually different wavelengths—irradiating the first and second light according to the present embodiment—while irradiating the measurement wave onto the semiconductor X to be measured when the semiconductor X to be measured is in a second surface recombination velocity condition, a second difference measurement wave, which is a difference between a first reflected wave or a first transmitted wave of the measurement wave in the first region in the semiconductor X to be measured and a second reflected wave or a second transmitted wave of the measurement wave in the second region in the semiconductor X to be measured; a second S/D calculation step of obtaining the S/D in the second surface recombination velocity condition based on the second difference that was measured in the second difference measuring step; a surface recombination velocity calculation step of obtaining the face recombination velocity S based on the S/D in the second surface recombination velocity condition that was obtained in the second S/D calculation step; and a lifetime calculation step of calculating a carrier lifetime in the semiconductor X to be measured based on the surface recombination velocity S that was obtained in the surface recombination velocity calculation step.

Since the semiconductor carrier lifetime measuring apparatus A3 of this embodiment only needs to obtain the respective difference measurement waves in the first and second surface recombination velocity conditions as described above, there is no need to assume the value of the diffusion coefficient D in the semiconductor as the measured sample X, and the carrier lifetime can be measured more accurately in comparison to conventional technology.

Moreover, the semiconductor carrier lifetime measuring apparatus A3 of this embodiment comprises a discharge unit 106 which applies a corona discharge to the first and second regions of the measured sample X as an example of the surface recombination velocity condition changing unit which changes the surface recombination velocity condition of the measured sample X among a plurality of conditions. Thus, the semiconductor carrier lifetime measuring apparatus A3 of this embodiment can change the surface recombination velocity condition in the measured sample X from its first condition to the second condition based on the discharge unit 106, and the second recombination velocity condition can be realized with the corona discharge. Moreover, since the second surface recombination velocity condition is realized by the corona discharge, the physical-chemical behavior in the measured sample X can be returned to its original state by ending the application of the corona discharge. There is no need to perform any pretreatment for changing the surface recombination velocity condition, and there is substantially no change in the physical-chemical behavior before and after measuring the carrier lifetime. Thus, the carrier lifetime can be measured in the production line.

Moreover, under normal circumstances, before a semiconductor wafer is used, a natural oxide film is formed on its surface through washing treatment for removing contamination such as fouling. With the semiconductor carrier lifetime measuring apparatus A3 of this embodiment, since the natural oxide film that was exposed by the washing treatment becomes the first surface recombination velocity condition, the treatment for realizing the first surface recombination velocity condition can double as the foregoing washing treatment, and, when the measured sample X is a semiconductor wafer, the number of man-hours can be reduced.

Moreover, with the third embodiment of the example shown in FIG. 14, the detection unit 103 detected the reflected wave of the measurement wave that was irradiated onto the measured sample X. However, it may also be configured to use the first and second transmitted waves of the measurement wave that was irradiated onto the measured sample X. For example, the detection unit 103 may also be configured by providing a waveguide for guiding the first transmitted wave of the measurement wave, so that it does not interfere with the twelfth corona wire 1062A, in the vicinity of the rear face (rear face region) of the measured sample X facing the first region of the measured sample X onto which the measurement wave is irradiated, providing a waveguide for guiding the second transmitted wave of the measurement wave, so that it does not interfere with the twenty-second corona wire 1062B, in the vicinity of the rear face (rear face region) of the measured sample X facing the second region of the measured sample X onto which the measurement wave is irradiated, providing a synthesizing unit which generates the difference measurement wave, which is the difference between the first and second transmitted waves of the measurement wave that was guided by the respective waveguides, by using the first transmitted wave as is and the second transmitted wave as is, and guiding the difference measurement wave that was synthesized by the synthesizing unit to the mixer 1030 of the detection unit 103. Even with this kind of configuration, the semiconductor carrier lifetime measuring apparatus A3 can measure the bulk carrier lifetime τb based on each of the similar processes of measuring the reflected wave of the measurement wave.

Another embodiment is now explained.

(Fourth Embodiment)

As explained as a modified example of the semiconductor carrier lifetime measuring apparatus A1 of the first embodiment, if the measured sample X is a semiconductor wafer for use in photovoltaic cells (PV semiconductor wafer), it would be more practical to measure the characteristics of the PV semiconductor wafer in a state where light for generating power is being irradiated. The semiconductor carrier lifetime measuring apparatus A4 of the fourth embodiment further comprises a power-generating irradiation unit 107 which irradiates a power-generating light onto the measured sample X in order to more accurately measure the actual characteristics of the semiconductor wafer for use in photovoltaic cells (PV semiconductor wafer) in a state where light for generating power is being irradiated in the configuration of the semiconductor carrier lifetime measuring apparatuses A2, A3 of the second and third embodiments described above.

Here, the semiconductor carrier lifetime measuring apparatus A4 of the fourth embodiment having a configuration where the semiconductor carrier lifetime measuring apparatus A2 of the second embodiment further comprises the power-generating irradiation unit 107, is now explained, but the same explanation can also be applied to the semiconductor carrier lifetime measuring apparatus A4 of the fourth embodiment having a configuration where the semiconductor carrier lifetime measuring apparatus A3 of the third embodiment further comprises the power-generating irradiation unit 107.

Figure 16:
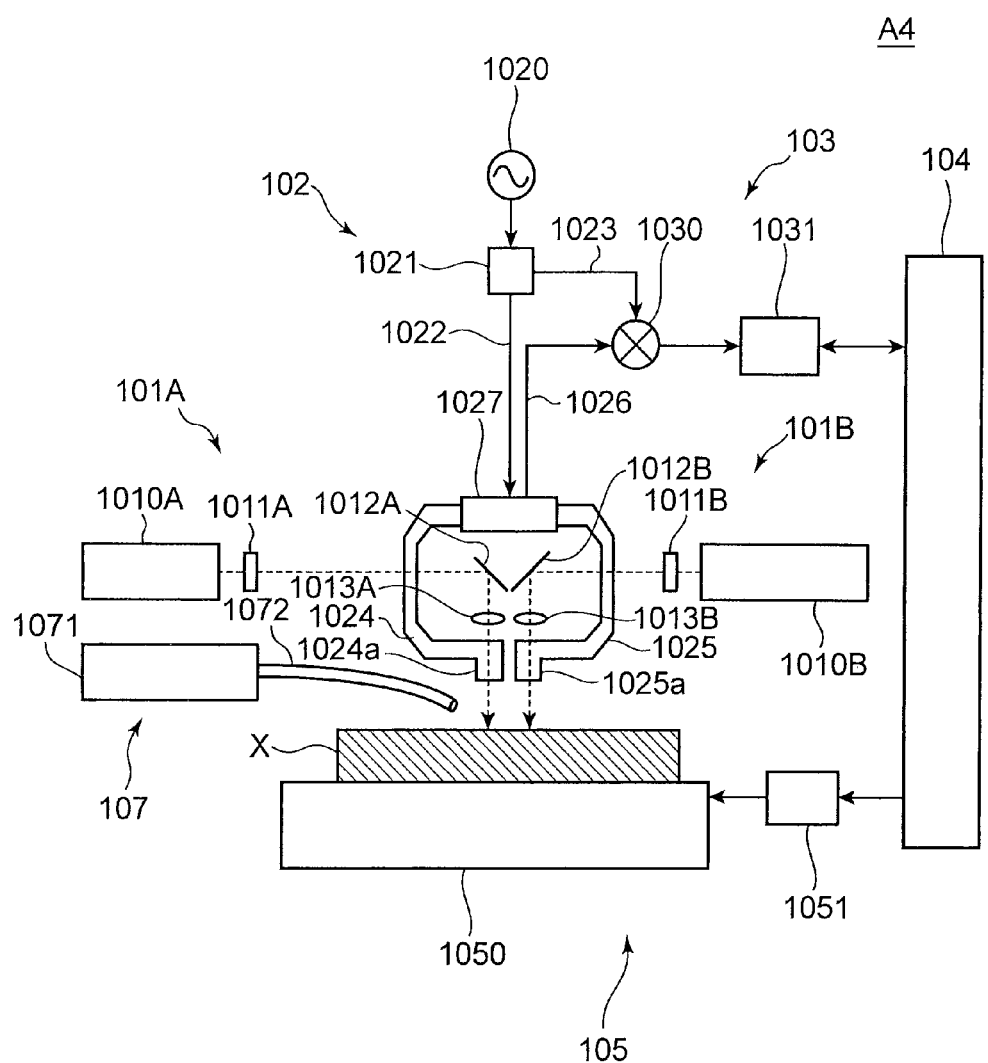
FIG. 16 is a diagram showing the configuration of the semiconductor carrier lifetime measuring apparatus in the fourth embodiment.

FIG. 16 is a diagram showing the configuration of the semiconductor carrier lifetime measuring apparatus in the fourth embodiment. In FIG. 16, the semiconductor carrier lifetime measuring apparatus A4 of the fourth embodiment is configured by comprising a light irradiation unit 101 (101A, 101B), a measurement wave I/O unit 102, a detection unit 103, a calculation control unit 104, a move part 105, and a power-generating irradiation unit 107. Since the light irradiation unit 101 (101A, 101B), the measurement wave I/O unit 102, the detection unit 103, the calculation control unit 104 and the move part 105 in the semiconductor carrier lifetime measuring apparatus A4 of the fourth embodiment are the same as the light irradiation unit 101 (101A, 101B), the measurement wave I/O unit 102, the detection unit 103, the calculation control unit 104 and the move part 105 in the semiconductor carrier lifetime measuring apparatus A2 of the second embodiment, the explanation thereof is omitted.

The power-generating irradiation unit 107 is configured by comprising a third light source unit 1071 which emits a power-generating light (bias light) having a predetermined spectral distribution which is pre-set according to the control of the calculation control unit 104, and a light-guiding member 1072 such as an optical fiber which guides the bias light emitted from the third light source unit 1071 toward the first and second regions of the measured sample X, and the bias light that was emitted from the third light source unit 1071 is irradiated on the first and second regions of the measured sample X via the light-guiding member 1072. Consequently, the PV semiconductor wafer as the measured sample X is biased by the power-generating light. The predetermined spectral distribution is arbitrarily decided according to the photoexcited carrier or the like of the PV semiconductor wafer to be measured. From the perspective of more accurately measuring the carrier lifetime of the PV semiconductor wafer using solar light, the third light source unit 1071 may be an illuminating device which illuminates light that emulates the same optical spectrum and irradiance as solar light. Moreover, from the foregoing perspective, the third light source unit 1071 preferably emits light corresponding to 1 SUN, and more preferably emits light having a simulated solar light spectrum. In the measurement of the bulk carrier lifetime, each of the foregoing processes is executed while the power-generating irradiation unit 107 irradiates the bias light onto the measured sample X. As a result of further comprising this kind of power-generating irradiation unit 107, the semiconductor carrier lifetime measuring apparatus A4 of this embodiment can more accurately measure the actual characteristics of the PV semiconductor wafer in a state where light is being irradiated for generating power.

In addition, since the specific resistance of the PV semiconductor wafer is varied across a relatively broad range, a diffusion coefficient in the light-irradiated state is required since light is irradiated onto the PV semiconductor wafer upon evaluating the actual power-generating characteristics, but it is difficult to estimate the diffusion coefficient of the PV semiconductor wafer. However, since the semiconductor carrier lifetime measuring apparatus A4 of the fourth embodiment having a configuration where the semiconductor carrier lifetime measuring apparatus A3 of the third embodiment further comprises the power-generating irradiation unit 107 operates as described the third embodiment, it can more accurately measure the bulk carrier lifetime τb in comparison to conventional technology.

The present specification discloses various modes of technology as described above, and the main technologies are summarized below.

The semiconductor carrier lifetime measuring apparatus according to one mode comprises a light irradiation unit which irradiates at least two types of light having mutually different wavelengths on a semiconductor to be measured, a measurement wave irradiation unit which irradiates a predetermined measurement wave onto the semiconductor to be measured, and a detection/calculation unit which detects a reflected wave of the measurement wave that has been reflected by the semiconductor to be measured or a transmitted wave of the measurement wave that has transmitted through the semiconductor to be measured, and which obtains a carrier lifetime in the semiconductor to be measured based on the detection results so as to minimize any error.

The semiconductor carrier lifetime measuring method according to another mode comprises a light irradiation step of irradiating at least two types of light having mutually different wavelengths on a semiconductor to be measured, a measurement wave irradiation step of irradiating a predetermined measurement wave onto the semiconductor to be measured, and a detection/calculation step of detecting a reflected wave of the measurement wave that has been reflected by the semiconductor to be measured or a transmitted wave of the measurement wave that has transmitted through the semiconductor to be measured, and obtaining a carrier lifetime in the semiconductor to be measured based on the detection results so as to minimize any error.

The semiconductor carrier lifetime measuring apparatus and the semiconductor carrier lifetime measuring method configured as described above can more accurately measure the carrier lifetime.

The semiconductor carrier lifetime measuring apparatus according to one mode comprises a light irradiation unit which irradiates at least two types of light having mutually different wavelengths on a semiconductor to be measured, a measurement wave irradiation unit which irradiates a predetermined measurement wave onto the semiconductor to be measured, a detection unit which detects a reflected wave of the measurement wave that has been reflected by the semiconductor to be measured or a transmitted wave of the measurement wave that has transmitted through the semiconductor to be measured, and a calculation unit which obtains a carrier lifetime in the semiconductor to be measured based on a first difference in a temporal relative change of the reflected wave or the transmitted wave detected by the detection unit as a result of the light irradiation unit irradiating the at least two types of light onto the semiconductor to be measured and the measurement wave irradiation unit irradiating the measurement wave onto the semiconductor to be measured when the semiconductor to be measured is in a first surface recombination velocity condition, and a second difference in a temporal relative change of the reflected wave or the transmitted wave detected by the detection unit as a result of the light irradiation unit irradiating the at least two types of light onto the semiconductor to be measured and the measurement wave irradiation unit irradiating the measurement wave onto the semiconductor to be measured when the semiconductor to be measured is in a second surface recombination velocity condition which is different from the first surface recombination velocity condition.

Moreover, the semiconductor carrier lifetime measuring method according to another mode comprises a light irradiation step of irradiating at least two types of light having mutually different wavelengths on a semiconductor to be measured, a measurement wave irradiation step of irradiating a predetermined measurement wave onto the semiconductor to be measured, a detection step of detecting a reflected wave of the measurement wave that has been reflected by the semiconductor to be measured or a transmitted wave of the measurement wave that has transmitted through the semiconductor to be measured, and a calculation step of obtaining a carrier lifetime in the semiconductor to be measured based on a first difference in a temporal relative change of the reflected wave or the transmitted wave detected in the detection step as a result of the at least two types of light being irradiated onto the semiconductor to be measured in the light irradiation step and the measurement wave being irradiated onto the semiconductor to be measured in the measurement wave irradiation step when the semiconductor to be measured is in a first surface recombination velocity condition, and a second difference in a temporal relative change of the reflected wave or the transmitted wave detected in the detection step as a result of the at least two types of light being irradiated onto the semiconductor to be measured in the light irradiation step and the measurement wave being irradiated onto the semiconductor to be measured in the measurement wave irradiation step when the semiconductor to be measured is in a second surface recombination velocity condition which is different from the first surface recombination velocity condition. Moreover, in another mode of the foregoing semiconductor carrier lifetime measuring method, preferably, in order to obtain the carrier lifetime based on the detection results with the semiconductor to be measured in the two conditions of the first and second surface recombination velocity conditions, in the calculation step, a carrier lifetime in the semiconductor to be measured is obtained by obtaining a ratio of a diffusion coefficient and a surface recombination velocity in the semiconductor to be measured based on the first difference and the second difference.

In addition, the semiconductor carrier lifetime measuring method according to another mode comprises a first difference measuring step of measuring, by irradiating at least two types of light having mutually different wavelengths while irradiating a predetermined measurement wave onto a semiconductor to be measured when the semiconductor to be measured is in a first surface recombination velocity condition, a first difference of a temporal relative change of a reflected wave of the measurement wave that has been reflected by the semiconductor to be measured or a transmitted wave of the measurement wave that has passed through the semiconductor to be measured, a first S/D calculation step of obtaining S/D in the first surface recombination velocity condition based on the first difference measured in the first difference measuring step when a surface recombination velocity in the semiconductor to be measured is defined as S and a diffusion coefficient is defined as D, a diffusion coefficient calculation step of obtaining the diffusion coefficient D based on the S/D in the first surface recombination velocity condition obtained in the first S/D calculation step, a surface recombination velocity condition changing step of causing the semiconductor to be measured to change from the first surface recombination velocity condition to a second surface recombination velocity condition that is different from the first surface recombination velocity condition, a second difference measuring step of measuring, by irradiating the at least two types of light having mutually different wavelengths while irradiating the measurement wave onto the semiconductor to be measured when the semiconductor to be measured is in a second surface recombination velocity condition, a second difference of a temporal relative change of a reflected wave of the measurement wave that has been reflected by the semiconductor to be measured or a transmitted wave of the measurement wave that has passed through the semiconductor to be measured, a second S/D calculation step of obtaining the S/D in the second surface recombination velocity condition based on the second difference measured in the second difference measuring step, a surface recombination velocity calculation step of obtaining the face recombination velocity S based on the S/D in the second surface recombination velocity condition obtained in the second S/D calculation step, and a lifetime calculation step of calculating a carrier lifetime in the semiconductor to be measured based on the surface recombination velocity S obtained in the surface recombination velocity calculation step.

With the semiconductor carrier lifetime measuring apparatus and the semiconductor carrier lifetime measuring method configured as described above, when the semiconductor to be measured is in a first surface recombination velocity condition, at least two types of light are irradiated onto the semiconductor to be measured and a measurement wave is irradiated onto the semiconductor to be measured, and the first difference of the temporal relative change of the reflected wave or the transmitted wave thereof is obtained, and, when the semiconductor to be measured is in a second surface recombination velocity condition that is different from the first surface recombination velocity condition, at least two types of light are irradiated onto the semiconductor to be measured and a measurement wave is irradiated onto the semiconductor to be measured, and the second difference of the temporal relative change of the reflected wave or the transmitted wave thereof is obtained, and the carrier lifetime of the semiconductor to be measured is obtained based on the foregoing first difference and second difference.

Accordingly, with the semiconductor carrier lifetime measuring apparatus and the semiconductor carrier lifetime measuring method configured as described above, since it will suffice if the first difference and the second difference are obtained as described above, it is possible to measure the carrier lifetime in the production line. In addition, without having to perform any pretreatment in advance as with conventional technology, it is possible to measure the carrier lifetime more accurately in comparison to conventional technology. Furthermore, since it will suffice if the first difference and the second difference are obtained as described above, there is no need to assume a value of the diffusion coefficient in the semiconductor to be measured, and the carrier lifetime can be measured more accurately in comparison to conventional technology.

Moreover, in another mode of the foregoing semiconductor carrier lifetime measuring apparatus, since it is better if the wavelength difference of the at least two types of light is greater, the at least two types of light are preferably a first light having a wavelength of an infrared region and a second light having a wavelength of an ultraviolet region, or the at least two types of light are preferably a first light having a wavelength of an infrared region and a third light having a wavelength of a visible region.

When light is irradiated onto a semiconductor, the light (incident light) will penetrate the semiconductor, but the length of penetration will depend on the wavelength of the incident light. According to the foregoing configuration, since the wavelength difference of the at least two types of light is great, the difference in the length of penetration will also increase. It is thereby possible to cause the ratio of influence, which is caused by the surface recombination contained in the reflected wave of the measurement wave or the transmitted wave of the measurement wave respectively based on the at least two types of light, to differ considerably. Thus, according to the foregoing configuration, the carrier lifetime can be measured more accurately in comparison to conventional technology.

Here, the length of penetration is the distance (depth) from the surface onto which light is irradiated onto the point where the light intensity of that light becomes 1/e of the incident intensity, and, normally, the length of penetration becomes longer (greater, deeper) as the optical wavelength is longer.

Moreover, in another mode, the foregoing semiconductor carrier lifetime measuring apparatus further comprises a surface recombination velocity condition changing unit which causes the semiconductor to be measured to change from the first surface recombination velocity condition to the second surface recombination velocity condition.

According to the foregoing configuration, the surface recombination velocity condition changing unit can be used to change the surface recombination velocity condition in the semiconductor to be measured from its first condition to its second condition.

Moreover, in another mode of the foregoing semiconductor carrier lifetime measuring apparatus, the surface recombination velocity condition changing unit is a corona discharge application unit which applies a corona discharge to a measurement wave irradiated region of the semiconductor onto which a measurement wave is irradiated by the measurement wave irradiation unit.

According to the foregoing configuration, the second recombination velocity condition can be realized with a corona discharge. In addition, since the second recombination velocity condition is realized with a corona discharge, the physical-chemical behavior in the semiconductor to be measured can be returned to its original state by ending the application of the corona discharge.

Moreover, in another mode of the foregoing semiconductor carrier lifetime measuring apparatus, the semiconductor to be measured is in a condition of being provided with a natural oxide film as the first surface recombination velocity condition.

Under normal circumstances, before a semiconductor wafer is used, a natural oxide film is formed on its surface through washing treatment for removing contamination such as fouling. According to the foregoing configuration, since the natural oxide film that was exposed by the washing treatment becomes the first surface recombination velocity condition, the treatment for realizing the first surface recombination velocity condition can double as the foregoing washing treatment, and the number of man-hours can be reduced.

Moreover, in another mode, the foregoing semiconductor carrier lifetime measuring apparatus further comprises a power-generating irradiation unit which irradiates a power-generating light onto the semiconductor to be measured.

According to the foregoing configuration, since a power-generating irradiation unit is provided, it is possible to more accurately measure the actual characteristics of the semiconductor to be measured in a state where light is irradiated for generating power.

Moreover, the semiconductor carrier lifetime measuring apparatus according to another mode comprises a light irradiation unit which irradiates at least two types of light having mutually different wavelengths onto mutually different first and second regions in a semiconductor to be measured, a measurement wave irradiation unit which irradiates a predetermined measurement wave onto the first and second regions, respectively, a difference measurement wave generation unit which generates a difference measurement wave, which is a difference between a first reflected wave of the measurement wave that has been reflected by the first region or a first transmitted wave of the measurement wave that has transmitted through the first region and a second reflected wave of the measurement wave that has been reflected by the second region or a second transmitted wave of the measurement wave that has transmitted through the second region, by using the first reflected wave or the first transmitted wave without modifying the same and using the second reflected wave or the second transmitted wave without modifying the same, a detection unit which detects a difference measurement wave generated by the difference measurement wave generation unit, and a calculation unit which obtains a carrier lifetime in the semiconductor to be measured based on a detection result detected by the detection unit.

In addition, the semiconductor carrier lifetime measuring method according to another mode comprises a light irradiating step in which at least two types of light having mutually different wavelengths are irradiated onto mutually different first and second regions in the semiconductor to be measured, a measurement wave irradiating step in which a predetermined wave is irradiated onto the first and second regions, respectively, a difference measurement wave generation step of generating a difference measurement wave, which is a difference between a first reflected wave of the measurement wave that has been reflected by the first region or a first transmitted wave of the measurement wave that has transmitted through the first region and a second reflected wave of the measurement wave that has been reflected by the second region or a second transmitted wave of the measurement wave that has transmitted through the second region, by using the first reflected wave or the first transmitted wave without modifying the same and using the second reflected wave or the second transmitted wave without modifying the same, a detection step of detecting a difference measurement wave generated in the difference measurement wave generation step, and a calculation step of obtaining a carrier lifetime in the semiconductor to be measured based on a detection result detected in the detection step.

With the semiconductor carrier lifetime measuring apparatus and method configured as described above, a difference measurement wave, which is a difference between a first reflected wave of the measurement wave that has been reflected by the first region or a first transmitted wave of the measurement wave that has transmitted through the first region and a second reflected wave of the measurement wave that has been reflected by the second region or a second transmitted wave of the measurement wave that has transmitted through the second region, is generated by using the first reflected wave or the first transmitted wave without modifying the same and using the second reflected wave or the second transmitted wave without modifying the same, the difference measurement wave is detected by the detector, and the carrier lifetime is obtained based on the detection results. Thus, since the number of significant figures of the detection results corresponding to the difference between the respective measurement results obtained by directly measuring the difference measurement wave with the detector will directly detect the difference measurement wave using the entire dynamic range in the detector than the number of significant figures in the difference between the respective measurement results that were calculated by obtaining the difference of the first measurement result obtained by measuring the first reflected wave or the first transmitted wave with a predetermined detector and the second measurement result obtained by measuring the second reflected wave or the second transmitted wave with the detector, there will be a greater number of significant figures. Accordingly, the semiconductor carrier lifetime measuring apparatus and method configured as described above can more accurately measure the carrier lifetime.

Moreover, in another mode of the foregoing semiconductor carrier lifetime measuring apparatus, the at least two types of light are two types of light selected among a first light having a wavelength of an infrared region, a second light having a wavelength of a visible region, and a third light having a wavelength of an ultraviolet region.

When light is irradiated onto a semiconductor, the light (incident light) will penetrate the semiconductor, but the length of penetration will depend on the wavelength of the incident light. According to the foregoing configuration, since the wavelength difference of the at least two types of light is great, the difference in the length of penetration will also increase. It is thereby possible to cause the ratio of influence, which is caused by the surface recombination contained in the reflected wave of the measurement wave or the transmitted wave of the measurement wave respectively based on the at least two types of light, to differ considerably. Thus, according to the foregoing configuration, the carrier lifetime can be measured more accurately in comparison to conventional technology.

Here, the length of penetration is the distance (depth) from the surface onto which light is irradiated onto the point where the light intensity of that light becomes 1/e of the incident intensity, and, normally, the length of penetration becomes longer (greater, deeper) as the optical wavelength is longer.

Moreover, in another mode, the foregoing semiconductor carrier lifetime measuring apparatus further comprises a light intensity control unit which controls at least one light intensity of at least two types of light having mutually different wavelengths so that initial first and second excess carrier masses that are generated when the at least two types of light are irradiated onto the first and second regions, respectively, become mutually equal.

According to the foregoing configuration, since the initial first and second excess carrier masses that are generated when the at least two types of light are irradiated onto the first and second regions, respectively, become mutually equal, for instance, the output signal level of the detector can be made to be zero in cases where the surface recombination velocity is zero, and the carrier lifetime can be measured even more accurately.

Moreover, in another mode, the foregoing semiconductor carrier lifetime measuring apparatus further comprises a surface recombination velocity condition changing unit which changes a surface recombination velocity condition in the semiconductor to be measured, and the calculation unit obtains a carrier lifetime in the semiconductor to be measured based on a first detection result detected by the detection unit when the semiconductor to be measured is in a first surface recombination velocity condition, and a second detection result detected by the detection unit when the semiconductor to be measured is in a second surface recombination velocity condition which is different from the first surface recombination velocity condition.

According to the foregoing configuration, when the semiconductor to be measured in the first surface recombination velocity condition, the first detection result is detected by the detection unit, and, when the semiconductor to be measured is in the second surface recombination velocity condition that is different from the first surface recombination velocity condition, the second detection result is detected by the detection unit, and the carrier lifetime in the semiconductor to be measured is obtained based on the foregoing first and second detection results. Accordingly, with the semiconductor carrier lifetime measuring apparatus configured as described above, it will sufficient if the first and second detection results are obtained as described above. Thus, it is not necessary to assume or measure the value of the diffusion coefficient in the semiconductor to be measured, and the carrier lifetime can be measured more easily and more accurately in comparison to conventional technology.

Moreover, in another mode of the foregoing semiconductor carrier lifetime measuring apparatus, the surface recombination velocity condition changing unit is a corona discharge application unit which applies a corona discharge to a measurement wave irradiated region of the semiconductor onto which a measurement wave is irradiated by the measurement wave irradiation unit.

According to the foregoing configuration, the second recombination velocity condition can be realized with a corona discharge. In addition, since the second recombination velocity condition is realized with a corona discharge, the physical-chemical behavior in the semiconductor to be measured can be returned to its original state by ending the application of the corona discharge. Thus, the semiconductor carrier lifetime measuring apparatus configured as described above can be used in a production line, and the production yield can be improved by sorting, during the production process, the semiconductor wafers that are unable to achieve the required specification (spec).

Moreover, in another mode of the foregoing semiconductor carrier lifetime measuring apparatus, the semiconductor to be measured is in a condition of being provided with a natural oxide film as the first surface recombination velocity condition.

Under normal circumstances, before a semiconductor wafer is used, a natural oxide film is formed on its surface through washing treatment for removing contamination such as fouling. According to the foregoing configuration, since the natural oxide film exposed by the washing treatment becomes the first surface recombination velocity condition, the treatment for realizing the first surface recombination velocity condition can double as the foregoing washing treatment, and the number of man-hours can be reduced.

Moreover, in another mode, the foregoing semiconductor carrier lifetime measuring apparatus further comprises a power-generating irradiation unit which irradiates a power-generating light onto the semiconductor to be measured.

According to the foregoing configuration, since a power-generating irradiation unit is provided, it is possible to more accurately measure the actual characteristics of the semiconductor to be measured in a state where light is irradiated for generating power. Accordingly, the semiconductor carrier lifetime measuring apparatus configured as described above can be suitably used, for example, for measuring the carrier lifetime of PV semiconductor wafers.

This application relates to and claims priority from Japanese Patent Application No. 2009-232880, filed on Oct. 6, 2009, and Japanese Patent Application No. 2010-103331, filed on Apr. 28, 2010, the entire disclosure of which is incorporated herein by reference.

The present invention has been appropriately and sufficiently explained above based on the embodiments with reference to the drawings in order to express the present invention, but it should be acknowledged that a person skilled in the art can easily change and/or improve the foregoing embodiments. Accordingly, so as long as the mode of change or the mode of improvement implemented by a person skilled in the art does not deviate from the scope of rights described in the scope of claims, it should be interpreted that such mode of change or mode of improvement is covered by the scope of claims of the present application.

Industrial Applicability

According to the present invention, it is possible to provide a semiconductor carrier lifetime measuring apparatus and a semiconductor carrier lifetime measuring method for measuring the carrier lifetime in a semiconductor.

The invention claimed is:

1. A semiconductor carrier lifetime measuring apparatus, comprising:
   a light irradiation unit which irradiates at least two types of light having mutually different wavelengths on a semiconductor to be measured;
   a measurement wave irradiation unit which irradiates a predetermined measurement wave onto the semiconductor to be measured; and
   a detection/calculation unit which detects a reflected wave of the measurement wave that has been reflected by the semiconductor to be measured or a transmitted wave of the measurement wave that has transmitted through the semiconductor to be measured, and which obtains a carrier lifetime in the semiconductor to be measured based on the detection results so as to minimize any error;
   wherein
   the detection/calculation unit comprises:
   a detection unit which detects a reflected wave of the measurement wave that has been reflected by the semiconductor to be measured or a transmitted wave of the measurement wave that has transmitted through the semiconductor to be measured; and
   a calculation unit which obtains a carrier lifetime in the semiconductor to be measured based on a first difference in a temporal relative change of the reflected wave or the transmitted wave detected by the detection unit as a result of the light irradiation unit irradiating the at least two types of light onto the semiconductor to be measured and the measurement wave irradiation unit irradiating the measurement wave onto the semiconductor to be measured when the semiconductor to be measured is in a first surface recombination velocity condition, and based on a second difference in a temporal relative change of the reflected wave or the transmitted wave detected by the detection unit as a result of the light irradiation unit irradiating the at least two types of light onto the semiconductor to be measured and the measurement wave irradiation unit irradiating the measurement wave onto the semiconductor to be measured when the semiconductor to be measured is in a second surface recombination velocity condition which is different from the first surface recombination velocity condition.

2. The semiconductor carrier lifetime measuring apparatus according to claim 1, wherein the at least two types of light are a first light having a wavelength of an infrared region and a second light having a wavelength of an ultraviolet region.

3. The semiconductor carrier lifetime measuring apparatus according to claim 1, wherein the at least two types of light are a first light having a wavelength of an infrared region and a third light having a wavelength of a visible region.

4. The semiconductor carrier lifetime measuring apparatus according to claim 1, further comprising:
   a surface recombination velocity condition changing unit which causes the semiconductor to be measured to change from the first surface recombination velocity condition to the second surface recombination velocity condition.

5. The semiconductor carrier lifetime measuring apparatus according to claim 4,
   wherein the surface recombination velocity condition changing unit is a corona discharge application unit which applies a corona discharge to a measurement wave irradiated region of the semiconductor onto which a measurement wave is irradiated by the measurement wave irradiation unit.

6. The semiconductor carrier lifetime measuring apparatus according to claim 4, wherein the semiconductor to be measured is in a condition of being provided with a natural oxide film as the first surface recombination velocity condition.

7. The semiconductor carrier lifetime measuring apparatus according to claim 1, further comprising:
   a power-generating irradiation unit which irradiates a power-generating light onto the semiconductor to be measured.

8. A semiconductor carrier lifetime measuring method, comprising:
   a light irradiation step of irradiating at least two types of light having mutually different wavelengths on a semiconductor to be measured;
   a measurement wave irradiation step of irradiating a predetermined measurement wave onto the semiconductor to be measured; and
   a detection/calculation step of detecting a reflected wave of the measurement wave that has been reflected by the semiconductor to be measured or a transmitted wave of the measurement wave that has transmitted through the semiconductor to be measured, and obtaining a carrier lifetime in the semiconductor to be measured based on the detection results so as to minimize any error;
   wherein
   the detecting/calculation step comprises:
   a detection step of detecting a reflected wave of the measurement wave that has been reflected by the semiconductor to be measured or a transmitted wave of the measurement wave that has transmitted through the semiconductor to be measured; and
   a calculation step of obtaining a carrier lifetime in the semiconductor to be measured based on a first difference in a temporal relative change of the reflected wave or the transmitted wave detected in the detection step as a result of the at least two types of light being irradiated onto the semiconductor to be measured in the light irradiation step and the measurement wave being irradiated onto the semiconductor to be measured in the measurement wave irradiation step when the semiconductor to be measured is in a first surface recombination velocity condition, and a second difference in a temporal relative change of the reflected wave or the transmitted wave detected in the detection step as a result of the at least two types of light being irradiated onto the semiconductor to be measured in the light irradiation step and the measurement wave being irradiated onto the semiconductor to be measured in the measurement wave irradiation step when the semiconductor to be measured is in a second surface recombination velocity condition which is different from the first surface recombination velocity condition.

9. The semiconductor carrier lifetime measuring method according to claim 8, wherein, in the calculation step, a carrier lifetime in the semiconductor to be measured is obtained by obtaining a ratio of a diffusion coefficient and a surface recombination velocity in the semiconductor to be measured based on the first difference and the second difference.

10. A semiconductor carrier lifetime measuring method, comprising:
   a first difference measuring step of measuring, by irradiating at least two types of light having mutually different wavelengths while irradiating a predetermined measurement wave onto a semiconductor to be measured when the semiconductor to be measured is in a first surface recombination velocity condition, a first difference of a temporal relative change of a reflected wave of the measurement wave that has been reflected by the semiconductor to be measured or a transmitted wave of the measurement wave that has passed through the semiconductor to be measured;
   a first S/D calculation step of obtaining S/D in the first surface recombination velocity condition based on the first difference measured in the first difference measuring step when a surface recombination velocity in the semiconductor to be measured is defined as S and a diffusion coefficient is defined as D;
   a diffusion coefficient calculation step of obtaining the diffusion coefficient D based on the S/D in the first surface recombination velocity condition obtained in the first S/D calculation step;
   a surface recombination velocity condition changing step of causing the semiconductor to be measured to change from the first surface recombination velocity condition to a second surface recombination velocity condition that is different from the first surface recombination velocity condition;
   a second difference measuring step of measuring, by irradiating the at least two types of light having mutually different wavelengths while irradiating the measurement wave onto the semiconductor to be measured when the semiconductor to be measured is in a second surface recombination velocity condition, a second difference of a temporal relative change of a reflected wave of the measurement wave that has been reflected by the semiconductor to be measured or a transmitted wave of the measurement wave that has passed through the semiconductor to be measured;
   a second S/D calculation step of obtaining the S/D in the second surface recombination velocity condition based on the second difference measured in the second difference measuring step;
   a surface recombination velocity calculation step of obtaining the face recombination velocity S based on the S/D in the second surface recombination velocity condition obtained in the second S/D calculation step; and
   a lifetime calculation step of calculating a carrier lifetime in the semiconductor to be measured based on the surface recombination velocity S obtained in the surface recombination velocity calculation step.

* * * * *